(12) United States Patent
Kojima et al.

(10) Patent No.: US 8,211,040 B2
(45) Date of Patent: Jul. 3, 2012

(54) CONTINUOUS SWALLOWING MOVEMENT MEASURING DEVICE AND METHOD FOR MEASURING A CONTINUOUS SWALLOWING MOVEMENT

(75) Inventors: Hidetoshi Kojima, Yaizu (JP); Hirotaka Kaneda, Yaizu (JP); Toyohiko Hayashi, Niigata (JP)

(73) Assignee: Sapporo Breweries Limited, Tokyo (JP)

( * ) Notice: Subject to any disclaimer, the term of this patent is extended or adjusted under 35 U.S.C. 154(b) by 601 days.

(21) Appl. No.: 11/659,421

(22) PCT Filed: Jul. 29, 2005

(86) PCT No.: PCT/JP2005/013969
§ 371 (c)(1),
(2), (4) Date: May 3, 2007

(87) PCT Pub. No.: WO2006/013797
PCT Pub. Date: Feb. 9, 2006

(65) Prior Publication Data
US 2009/0030346 A1 Jan. 29, 2009

(30) Foreign Application Priority Data

Aug. 5, 2004 (JP) ................................ 2004-229079
Sep. 2, 2004 (JP) ................................ 2004-255966
Feb. 18, 2005 (JP) ................................ 2005-042545

(51) Int. Cl.
*A61B 5/11* (2006.01)
(52) U.S. Cl. ...................................................... 600/590
(58) Field of Classification Search .................... 600/590
See application file for complete search history.

(56) References Cited

U.S. PATENT DOCUMENTS 4,303,077 A * 12/1981 Lewin et al. .................. 600/590
4,629,424 A 12/1986 Lauks et al.

FOREIGN PATENT DOCUMENTS

EP 0 444 594 A1 9/1991
FR 2 800 266 A1 5/2001
(Continued)

OTHER PUBLICATIONS

Hayashi et al. "Relationship between Rice-Gruel Properties and Swallowing Motion" as submitted by applicant.*

(Continued)

*Primary Examiner* — Max Hindenburg
*Assistant Examiner* — Renee Danega
(74) *Attorney, Agent, or Firm* — Oblon, Spivak, McClelland, Maier & Neustadt, L.L.P.

(57) ABSTRACT

A continuous swallowing movement measuring device includes pressure sensors placed in a line along a direction of an up and down movement of a thyroid cartilage when a food is swallowed, a first one of the pressure sensors placed at a top position of the thyroid cartilage, a second one of the pressure sensors placed along the direction to measure swallows included in a continuous swallowing movement. The device also includes a tool for wearing the pressure sensors and for fixing the pressure sensors to touch an anterior region of a neck of a subject. The tool includes a fixing unit fixes the pressure sensors. The tool also includes a supporter of the pressure sensors supports the fixing unit. Further, the tool includes a holding band holds the supporter of the pressure sensors on the anterior region of the neck of the subject.

8 Claims, 25 Drawing Sheets

FOREIGN PATENT DOCUMENTS

| | | | |
|---|---|---|---|
| JP | 6 90956 | | 4/1994 |
| JP | 2003 111748 | | 4/2003 |
| JP | 2006 95264 | | 4/2006 |
| WO | WO 01/15743 | * | 7/2000 |

OTHER PUBLICATIONS

Vaiman et al. "Surface electromyographic studies of swallowing in normal children, age 4-12 years" Sep. 2003. pp. 65-73.*

Vaiman et al. "Surface electromyographic studies of swallowing in normal children, age 4-12 years" International Journal of Pediatric Otorhinolaryngology, Jan. 2004. p. 65-73.*

Hayashi et al. "Relationship Between Rice-Gruel Properties and Swallowing Motion" 2002. PTO translation Sep. 2010.*

Kaneko, H. et al., "Evaluation of Swallowing Function by Simultaneous Measurement of Larynx Movement, Electromyogram of Suprahyoid Musculature and Swallowing Sound", Technical Report of IEICE, vol. 101, No. 478, pp. 135-142, 2001.

Hayashi, T. et al.,"Relationship Between Rice-Gruel Properties and Swallowing Motion", The Japanese Society of Dysphagia Rehabilitation, vol. 6, No. 2, pp. 187-195, 2002. (with English abstract).

Kojima, H. et al.,"Inryo Inyoji no Enge Katsudo Keisoku System no Kaihatsu", Nippon Shokuhin Kagaku Kogakukai Dai 51 Kai Taikai Koenshu, p. 65 (2Ha7), 2004.

* cited by examiner (a) BEFORE AND AFTER OF SWALLOWING
(b) DURING SWALLOWING

FIG.6
(a)
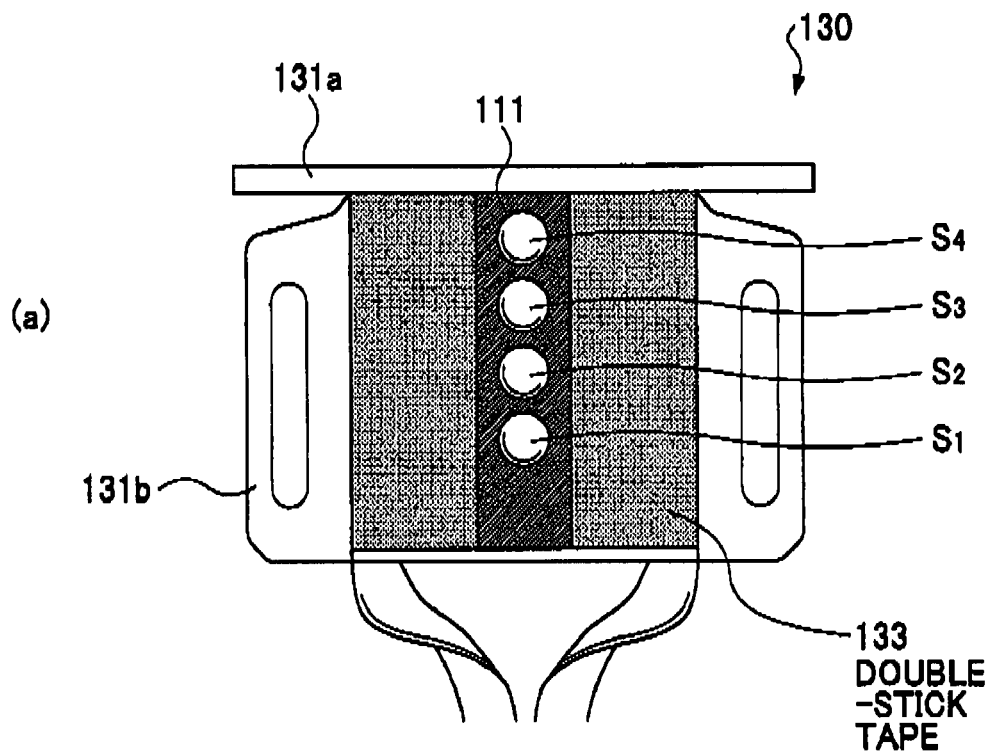
(b)
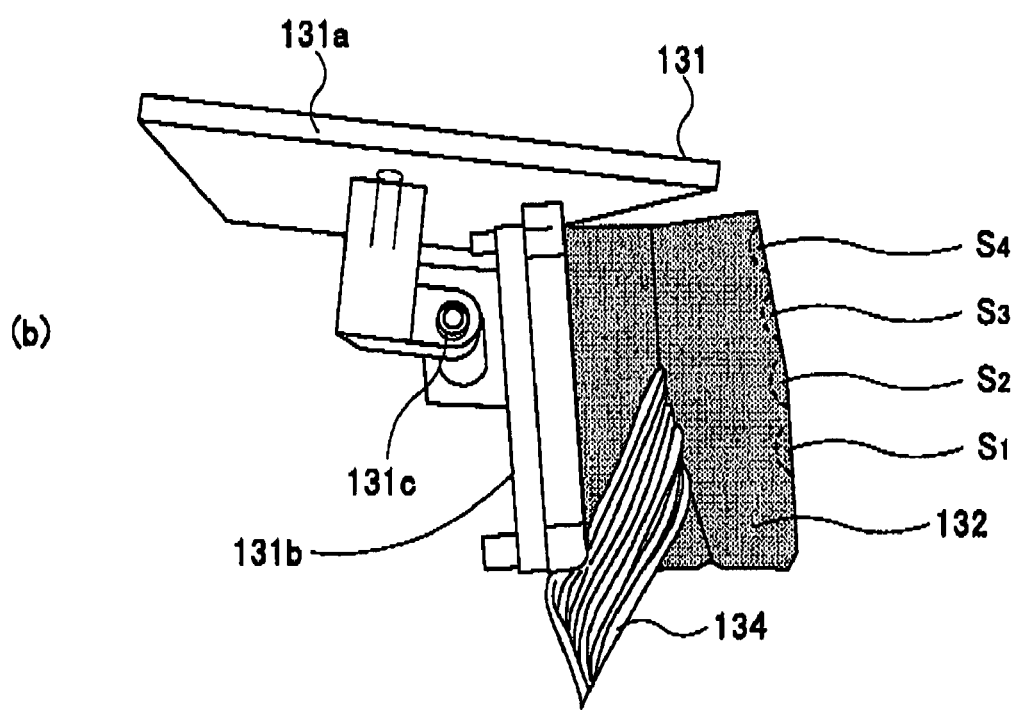

FIG.11
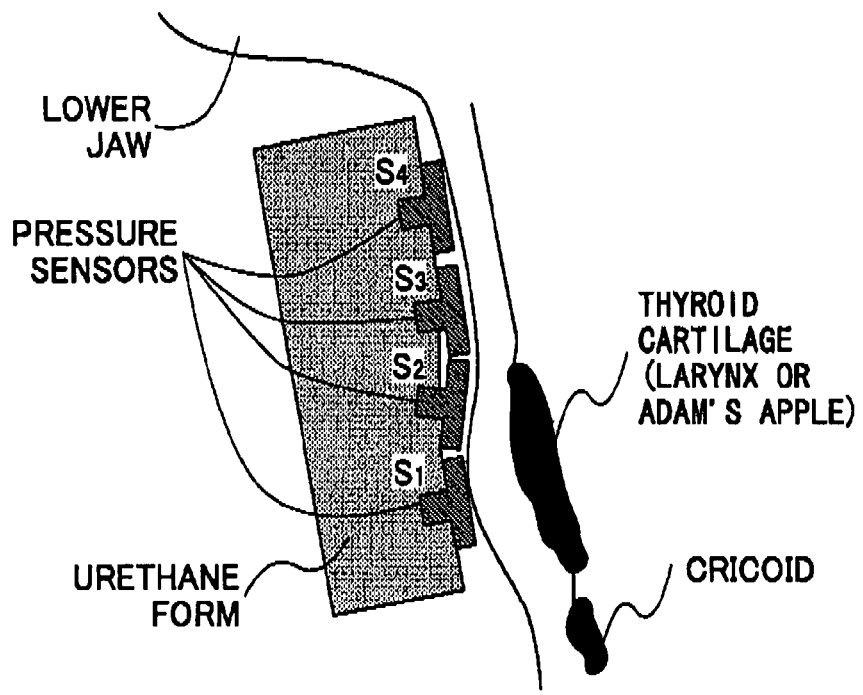
(a) BEFORE AND AFTER OF SWALLOWING
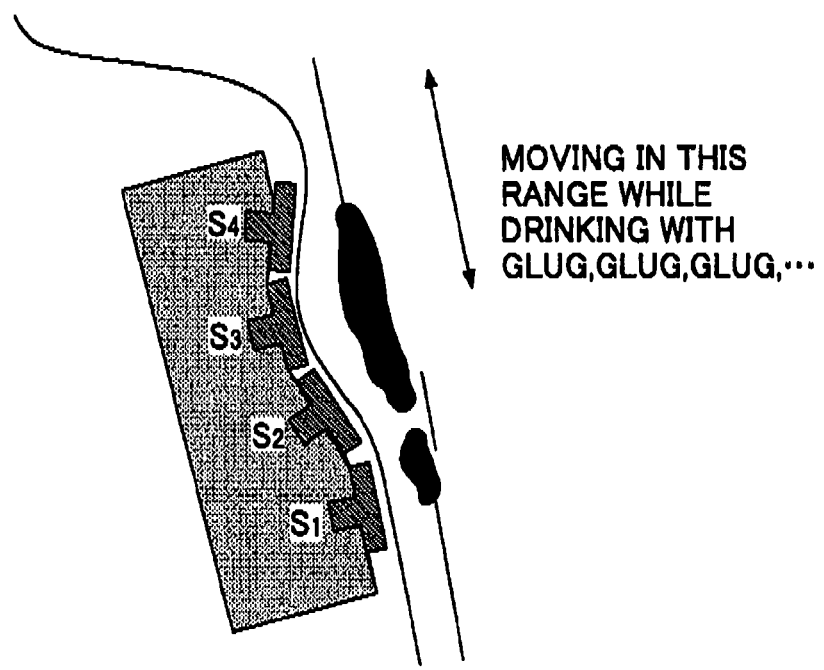
(b) DURING SWALLOWING

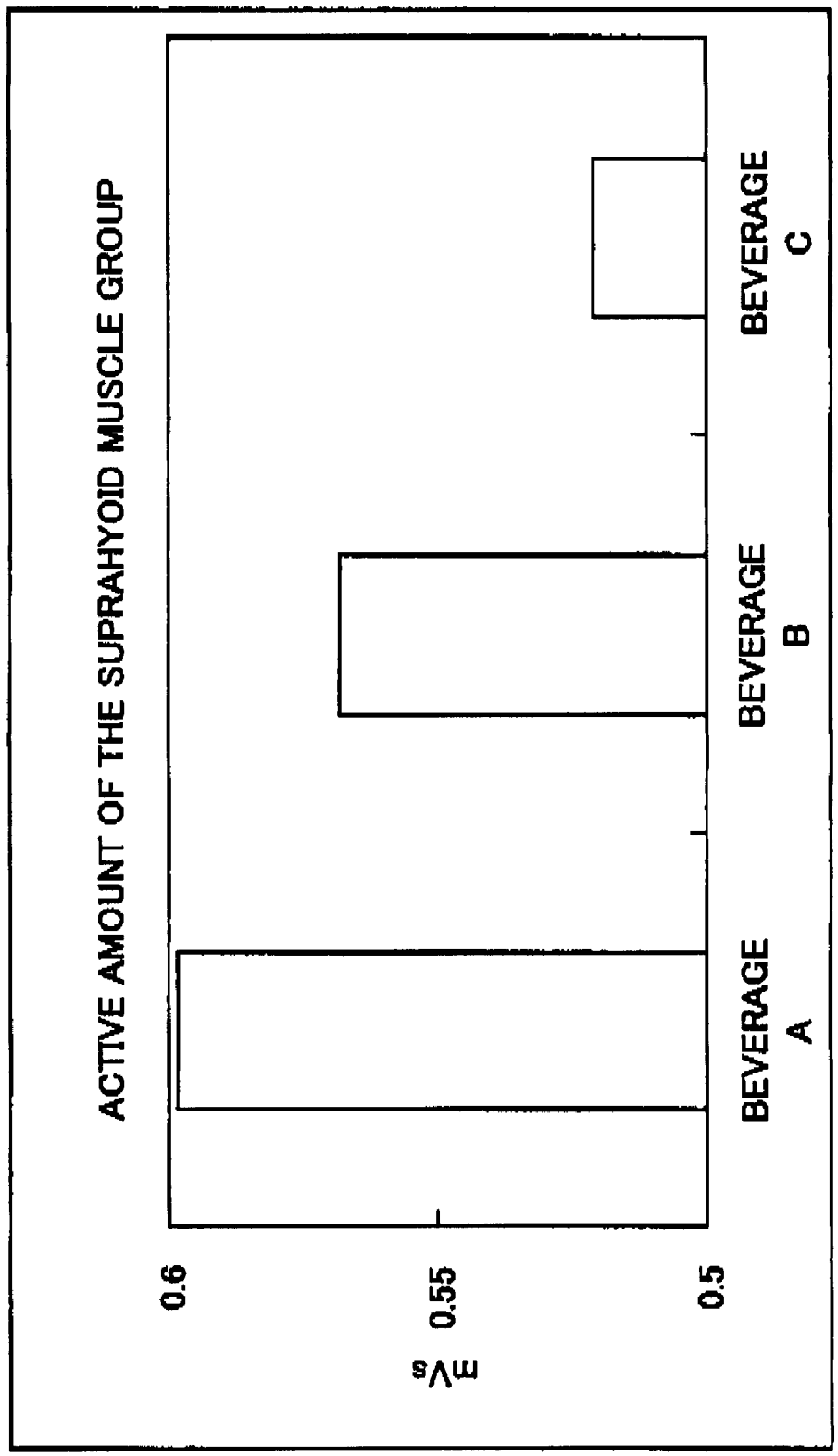

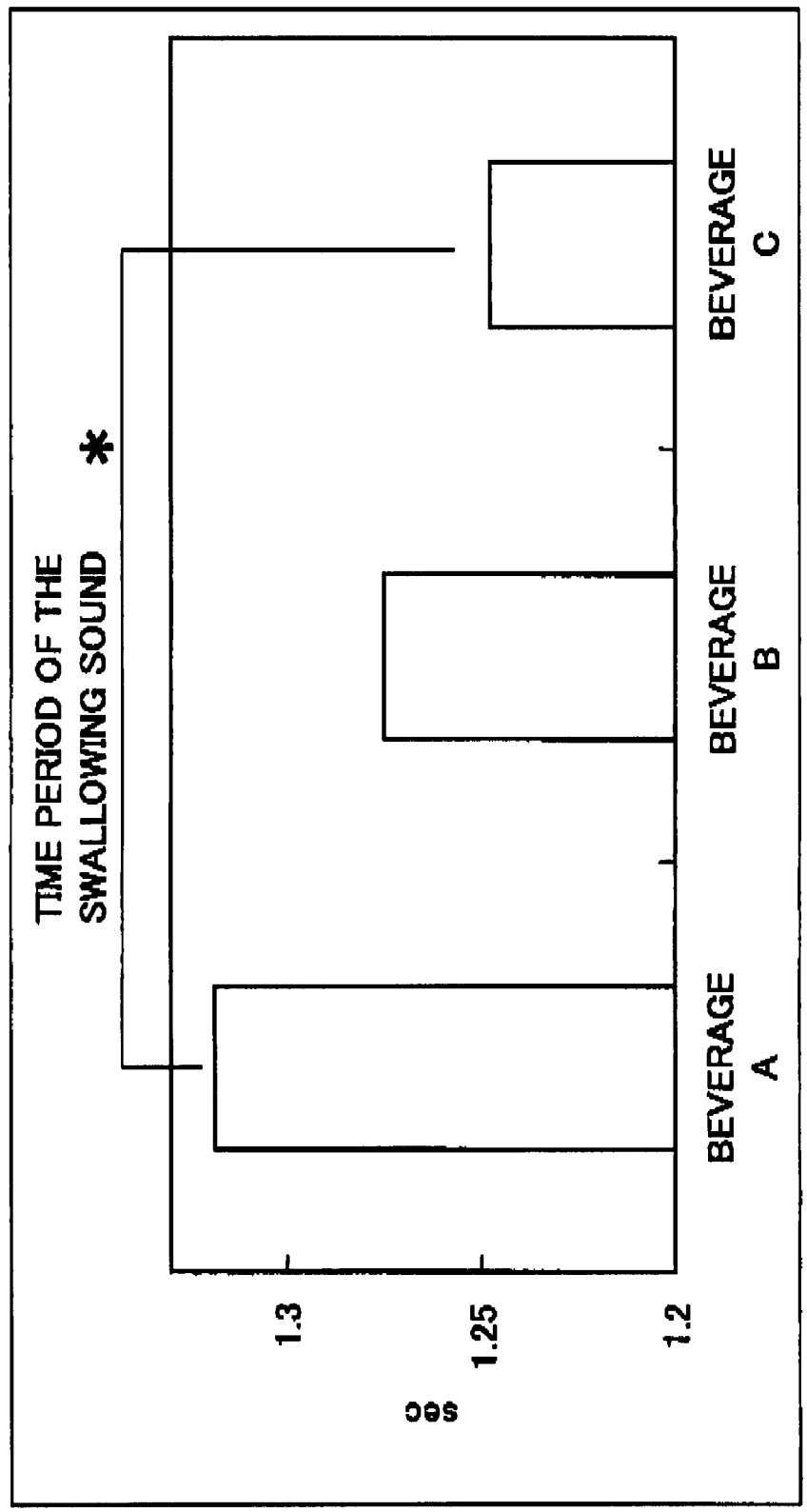

FIG.24
(a)
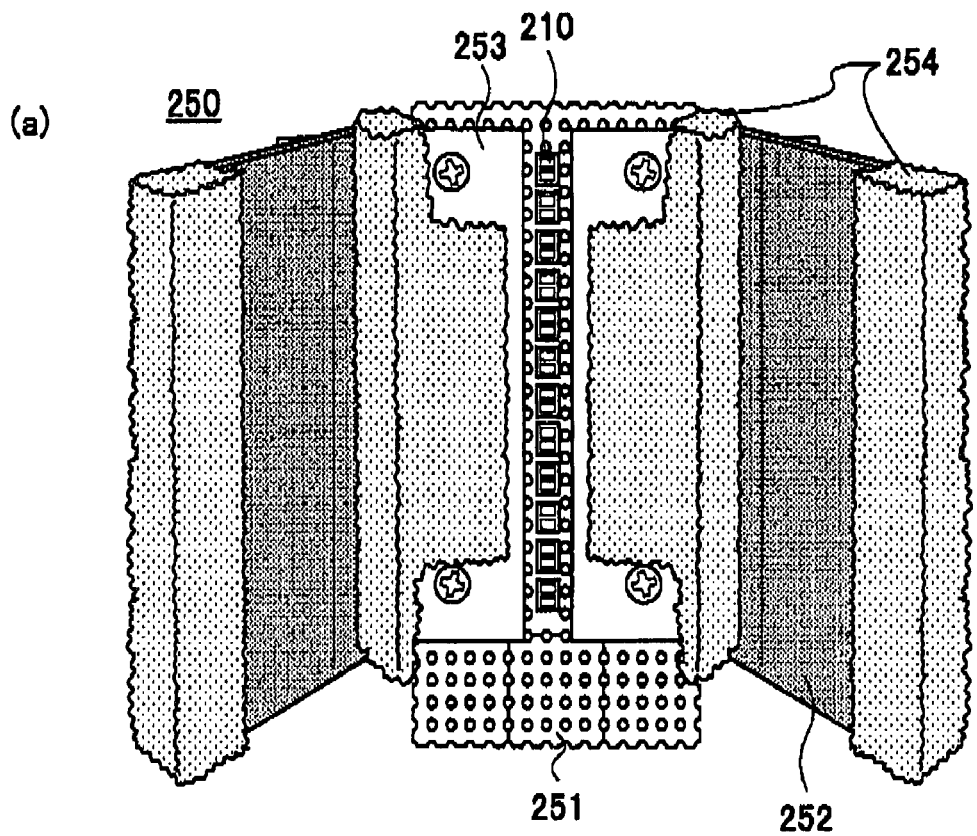
(b)
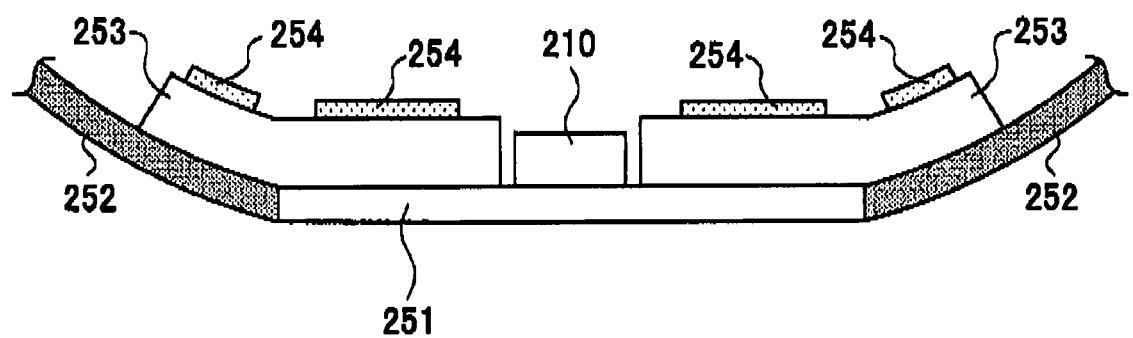

FIG. 27
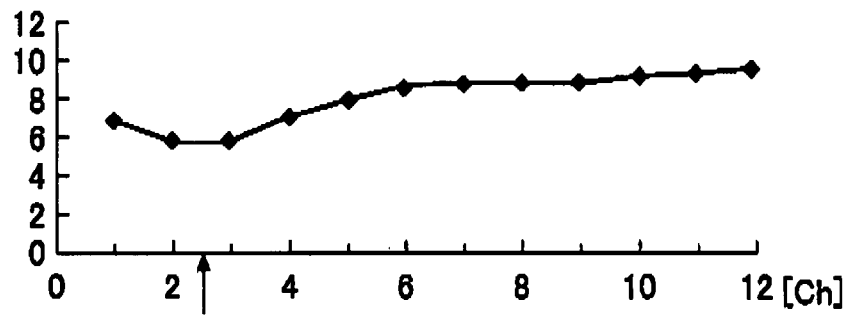
(a) BEFORE SWALLOWING
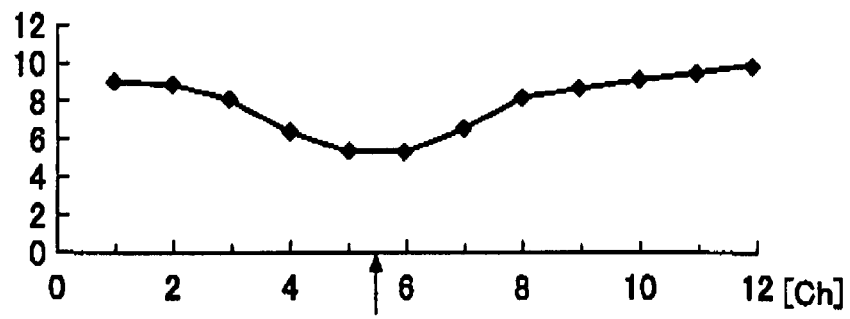
(b) DURING SWALLOWING (1)
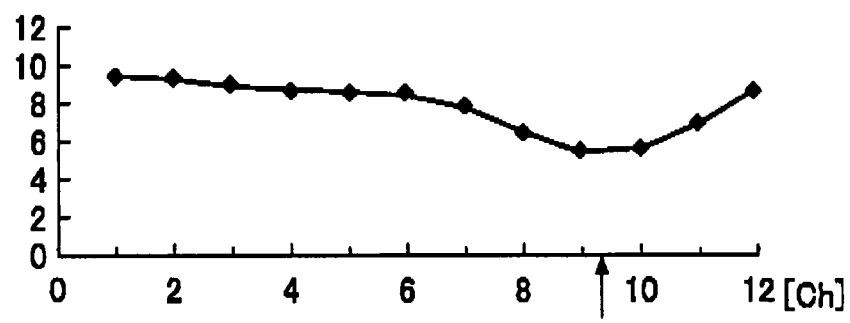
(c) DURING SWALLOWING (2)

CONTINUOUS SWALLOWING MOVEMENT MEASURING DEVICE AND METHOD FOR MEASURING A CONTINUOUS SWALLOWING MOVEMENT

BACKGROUND OF THE INVENTION

1. Field of the Invention

This invention generally relates to a measuring device of a swallowing movement which movement occurs at the throat when a person swallows a drink such as beer and a method for measuring the swallowing movement.

2. Description of the Related Art

In conjunction with the movement when a person swallows food, a trial to measure real swallowing movement has been done for the purposes of evaluating a characteristic of food and the swallowing ability of a person.

As the method for evaluating and measuring the swallowing movement, that is, a movement to swallow food, there are diagnostic imaging methods such as a VF method (video X-ray test) and an ultrasonography test. The VF method is such that a subject swallows food including contrast media, and an X-ray motion image from the oral cavity, the pharynx, to the upper esophagus is recorded and it is observed. The ultrasonography test is where a supersonic wave dislocation device is used, and a probe is placed in a cervical part from the lower jaw, and an organ in the oral cavity and an adduction movement of the vocal cords are observed and evaluated in real time. However, in these methods, a direct diagnosis by a picture can be performed, but the swallowing movement cannot be quantified. Therefore, when these are utilized in medical treatments and rehabilitation, it is necessary to evaluate a symptom time-wise and quantitatively to set a treatment policy depending on the symptom to change, but they cannot be utilized to perform such an evaluation. Also, X-rays cannot be used for a physically unimpaired person except a person who is a treatment object, so that a test/a measurement method with the above X-rays can not be utilized for the measurement of the swallowing movement to study such as a feeling at the throat at the time of swallowing a drink and an easiness to swallow food.

In these days, as the method for measuring the swallowing movement that deals with this point, a detecting element with the use of plural pressure sensors is stuck on an anterior region of neck, and a device measuring a larynx vertical motion at the time of swallowing quantitatively has been developed and examined (for example, please see the non-patent document 1).

FIG. 1 is a structural view of a device 1 for measuring the swallowing movement which is developed for measuring the larynx motion, an electromyogram of the suprahyoid muscle group and a swallowing sound at the time of swallowing food.

As shown in FIG. 1, the device 1 comprises a measurement part 10 and an analysis part 20. The measurement part 10 includes a pressure sensor 11, a myogenic potential electrometer electrode 12 and a microphone 13. The pressure sensor 11 is connected to a distorted amplifier 14, the myogenic potential electrometer electrode 12 is connected to an electromyography 15, and the microphone 13 is connected to a charge amplifier 16.

The analysis part 20 comprises an A/D converter 21 which transforms analog signals output by the distorted amplifier 14, the electromyography 15 and the charge amplifier 16 into corresponding digital signals and a personal computer 22 which performs various operations and processes signals from the converter 21.

This system measures at the same time the vertical motion of the thyroid cartilage (that is, the Adam's apple) which is a part of the larynx by the pressure sensor 11, the muscle's activity of the suprahyoid muscles group by the myogenic potential electrometer electrode 12, and a swallowing sound by the microphone 13.

As shown in FIG. 2, the pressure sensor 11 is such that three pairs of sensors become pairs in right and left lengthwise directions (up and down directions), so that six sensors in total are fixed in an urethane foam 11a, which foam is attached to a resin basal part 11b. When the urethane foam 11a is attached to the neck, double-stick tapes are stuck on the urethane foam 11a to be able to fix the urethane foam 11a on the neck. Also, a band 11d is attached on the resin basal part 11b, and sensors are attached in the cervical part by using the band so that sensors are located in the anterior region of neck.

A myogenic potential electrometer electrode (surface electrode) 12 is affixed to an equivalency region of the mylohyoid muscle of the digastric muscle, reference electrodes (standard electrode) are attached to both earlobes. When a thing is swallowed, the device 12 can measure how much force is applied by muscles. A muscle to measure is the suprahyoid muscle group.

The microphone 13 is attached such that the microphone is located beside the cricoid.

FIG. 3 is a view explaining the attachment of the pressure sensor 11 to the anterior region of the neck and the detection principle of the swallowing movement. Also, FIG. 4 is a view showing signal waves obtained from the pressure sensor 11, the myogenic potential electrometer electrode 12, and the microphone 13.

As shown in FIG. 3, the pressure sensor 11 is attached such that among three pairs of sensors, the lowest sensor is located in the normal position which position has no swallowing movement at the thyroid cartilage.

Referring to FIGS. 3 and 4, the swallowing movement when a lump of food is poured into the pharynx from the oral cavity is explained.

First of all, when the lump of food is poured from the oral cavity with the tongue, the suprahyoid muscle group begins an activity as shown in the myogenic potential electrometer output (p1). Following it, the thyroid cartilage which is a part of the larynx begins to rise (FIG. 3 (a)). An output voltage of the pair 2 of the pressure sensor rises (p3); thereby, the pair 3 of the pressure sensor rises (p4) next. At the time of a movement to the lower part of the larynx, it is shown to that vice versa and the thyroid cartilage returns to the original position (p7). As shown in the output wave, after starting the pharynx rising, the swallowing sound obtained from the microphone is begun in a few seconds (p8).

As described the above, the pharynx movement, the electromyogram of the suprahyoid muscle group and the swallowing sound of the swallowing movement when food is swallowed are taken out as electrical signals with the swallowing movement measuring device. For example, the capability to perform an analysis and an evaluation such as a change that occurs due to a kind of food or a difference by a person swallowing is expected.

Non-Patent Document 1: Toyohiko Hayashi et al., "A relationship between a property of rice gruel and a swallowing change—Evaluation by a simultaneous measurement of pharynx movement/EMG/swallowing sound", Japan A feeding/Swallowing Rehabilitation Study Group Magazine 6 (2): 0-0, 2002.

SUMMARY OF THE INVENTION

On the other hand, among foods, for beverages like beer, senses such as feeling at the throat at the time of swallowing a drink, an easiness to swallow and drinkability are important evaluation items in order to evaluate characteristics of commercial products. For example, it is said that "beer is tasted with feeling at the throat at the time of swallowing the drink", so that beer is noticeable as sounding at the throat with gurgling while drinking.

In order to study to be able to evaluate objectively senses of persons with such a swallowing movement, the present inventors studied whether the above swallowing movement measuring device can be utilized. As a result, the above measuring device was improved, and a device which can measure the larynx movement when a drink such as beer is swallowed continually with "glug, glug, glug, . . . ". (hereinafter, it is described as "continuous swallowing movement") has been developed. That is, the present invention is an improvement of the above measuring device and is able to measure the continuous swallowing movement with "glug, glug, glug, . . . ", compared to the conventional measuring device which measures one swallowing movement.

According to the study of the present inventors, different from one swallowing movement, the larynx's position has vertical motion as above in the continuous swallowing movement, and it is recognized that the movement of the larynx cannot be accurately measured in the above conventional measuring device. Also, a position of the detecting element slips off by means of one swallowing movement and the measurement of the continuous movement is impossible for the attaching method of the detection element of the conventional measuring device. Therefore, in the present invention, the detecting element is improved, and the measurement of the continuous swallowing movement is possible. At the same time, the fixing method to a subject wearing the detecting element is improved, and an attaching position of the detecting element does not slip off due to the continuous swallowing movement.

MEANS FOR SOLVING PROBLEM

A continuous swallowing movement measuring device of the present invention comprising:
plural pressure sensors placed in line along a direction of the up and down movement of thyroid cartilage when food is swallowed; and
a tool for wearing the pressure sensor for fixing the pressure sensors by touching on a anterior region of neck of a subject;
wherein the tool for wearing the pressure sensor is provided with fixing means for fixing the pressure sensor, a supporter of the pressure sensor supporting the fixing means and a holding band holding the supporter of the pressure sensor on the anterior region of neck of the subject.

Another aspect of the present invention is that a continuous swallowing movement measuring device comprises:
plural pressure sensors placed in line along a direction of the up and down movement of thyroid cartilage when food is swallowed; and
a tool for wearing the pressure sensor for fixing the pressure sensors by touching on a anterior region of neck of a subject;
wherein the tool for wearing the pressure sensor is provided with fixing means for fixing the pressure sensor, a supporter of the pressure sensor supporting the fixing means and a holding band holding the supporter of the pressure sensor on the anterior region of neck of the subject,
wherein the continuous swallowing movement measuring device is also provided with a myogenic potential electrometer for measuring a force to act on the suprahyoid muscle group of the subject and a vibration pickup for measuring a swallowing sound.

Also, another aspect of the present invention is that a method for continuous swallowing movement comprises:
a mounting step, in which a tool for wearing plural pressure sensors is fixed by touching on a anterior region of neck of a subject so that the lowest sensor among the plural pressure sensors is placed near the thyroid cartilage of the subject; wherein the tool for wearing the plural pressure sensors supports the plural pressure sensors including pressure sensors recognizing a position of the thyroid cartilage on the upper limit position or near the upper limit position of the thyroid cartilage at the time of continuous swallowing movement and is provided with the plural pressure sensors along a direction of up and down movement of the thyroid cartilage;
a reading step for reading changes of an output signal from each pressure sensor when the subject drinks beverages continuously; and
a measuring step for measuring up and down movement of the thyroid cartilage of the subject when the subject drink beverages continuously based on a period of an output signal peak from each pressure sensor.

Also, another aspect of the present invention is that a method for continuous swallowing movement comprises:
a step for fixing a surface electrode for measuring a myogenic potential by contacting on an equivalency region of the mylohyoid muscle of the digastric muscle of an anterior region of the neck of a subject;
a step for obtaining an electric signal which is generated by moving the suprahyoid muscle group from the surface electrode when the subject drinks beverages continuously; and
a step for determining a kinetic amount of the suprahyoid muscle group based on the obtained electric signal.

Also, another aspect of the present invention is that a method for continuous swallowing movement comprises:
a step for attaching a vibration pickup at a portion located beside a cricoid of an anterior region of the neck of a subject;
a step for measuring a swallowing sound from the vibration pickup when the subject drinks beverages continuously; and
a step for measuring a period of a peak of the measured value of the swallowing sound.

Also, another aspect of the present invention is that a continuous swallowing movement measuring device comprises:
plural reflection type optical sensors placed in line along a direction of the up and down movement of thyroid cartilage when food is swallowed; and
an optical sensor mounting device for fixing the optical sensors at a predetermined distance on a anterior region of the neck of a subject;
wherein the optical sensor mounting device is provided with a fixation board for fixing the optical sensors and a holding band holding the fixation board on the anterior region of the neck of the subject.

Also, another aspect of the continuous swallowing movement measuring device in the present invention is that the reflection type optical sensor has a light emitting element comprising an infrared light emitting diode and an infrared detection phototransistor.

In addition, another aspect of the present invention is that a method for continuous swallowing movement comprises:
a mounting step, in which an optical sensor mounting device is fixed by touching on a anterior region of the neck of a subject so that the lowest sensor among the plural optical sensors is placed near the thyroid cartilage of the subject; wherein the optical sensor mounting device supports plural reflection type optical sensors and is provided with the plural reflection type optical sensors in an arrangement along a direction of up and down movement of the thyroid cartilage;

a step for recognizing the distance between the optical sensor and a surface of the anterior region of the neck based on an output signal from each optical sensor when the subject drinks beverages continuously;

a step for reading a change of position at a minimized portion of the distance; and a step for measuring the up and down movement of the thyroid cartilage of the subject when the subject drinks beverages continuously based on a transfer period of the minimized portion.

According to the continuous swallowing movement measuring device and the continuous swallowing movement measuring method of the present invention, the measurement of the continuous swallowing movement is possible, and the same time, the attaching position of the detecting element does not slip off by means of the continuous swallowing movement, and the measurement of precise swallowing movement is enabled.

Also, by using the continuous swallowing movement measuring device of the present invention, the thyroid cartilage movement, the movement of the suprahyoid muscles group and swallowing sound at the time of continuously drinking beverages can be measured accurately. Also, applying these measured data to the evaluation and diagnosis of the swallowing movement of the subject contributes to a diagnosis capability for swallowing of a subject, as well as evaluation and development of food and drink.

In addition, according to the continuous swallowing movement measuring device using a reflection type optical sensor, by measuring the swallowing movement using an optical sensor with indirect pressure as opposed to the cervical part, wearing the cervical part of the measuring device disappears, and the swallowing movement can be measured in a more natural environment. Moreover, since each sensor is fixed on a fixed board, each sensor does not contact the laryngeal and sensors themselves do not move as the swallowing movement, so that the position of sensors is stable and the measurement with high accuracy can be attained.

BRIEF DESCRIPTION OF THE DRAWINGS

Other objects, features and advantages of the present invention will become more apparent from the following detailed description when read in conjunction with the accompanying drawings, in which:

FIG. 6 provides views showing a tool for wearing the pressure sensor;

FIG. 11 provides figures showing a relationship between the swallowing movement and the output of the pressure sensor;

FIG. 16 is a graph showing a relationship between the kinetic amount of the suprahyoid muscle group and alcoholic beverage with foaming properties;

FIG. 17 is a graph showing a relationship between time periods of swallowing sound and alcoholic beverage with foaming properties;

FIG. 24 is a view showing an optical sensor mounting device, where (a) shows a front elevation view and (b) shows a partial diagrammatic view of a sensor mounting part;

FIG. 27 is a view showing a relationship between the output of the optical sensor and the swallowing movement.

DESCRIPTION OF THE PREFERRED EMBODIMENTS

A description will now be given, with reference to the embodiments according to the present invention.

The embodiment according to the present invention is explained below referring to FIGS. 5-13.

Figure 5:
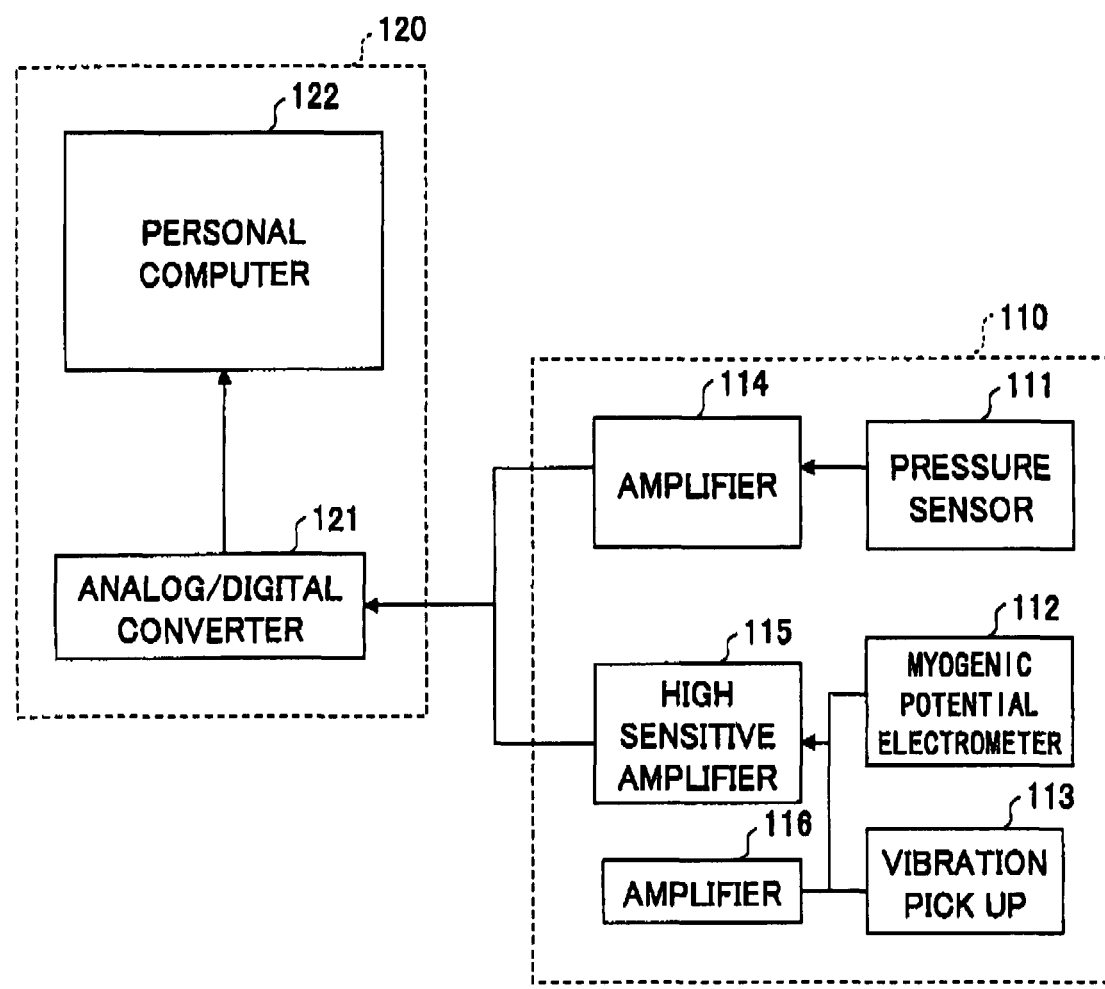
FIG. 5 is a block structural view of a swallowing movement measuring device which measures the swallowing movement of the embodiment of the present invention.

FIG. 5 is a block structural view of a swallowing movement measuring device 100 which measures the swallowing movement of the embodiment of the present invention. The basic structure of the swallowing movement measuring device 100 of the embodiment of the present invention is the same as the swallowing movement measuring device 1 and it is composed of the measurement part 110 and the analysis part 120. The measurement part 110 has the pressure sensor 111, the small living body electrode 112, and the vibration pickup (microphone) 113. The pressure sensor 111, the small living body electrode 112, and the vibration pickup (microphone) 113 are connected to amplifiers 114, 115 and 116, respectively. Also the measurement part 110 is input to the personal computer 122 via the analog digital converter 121 of the analysis part 120.

Figure 1:
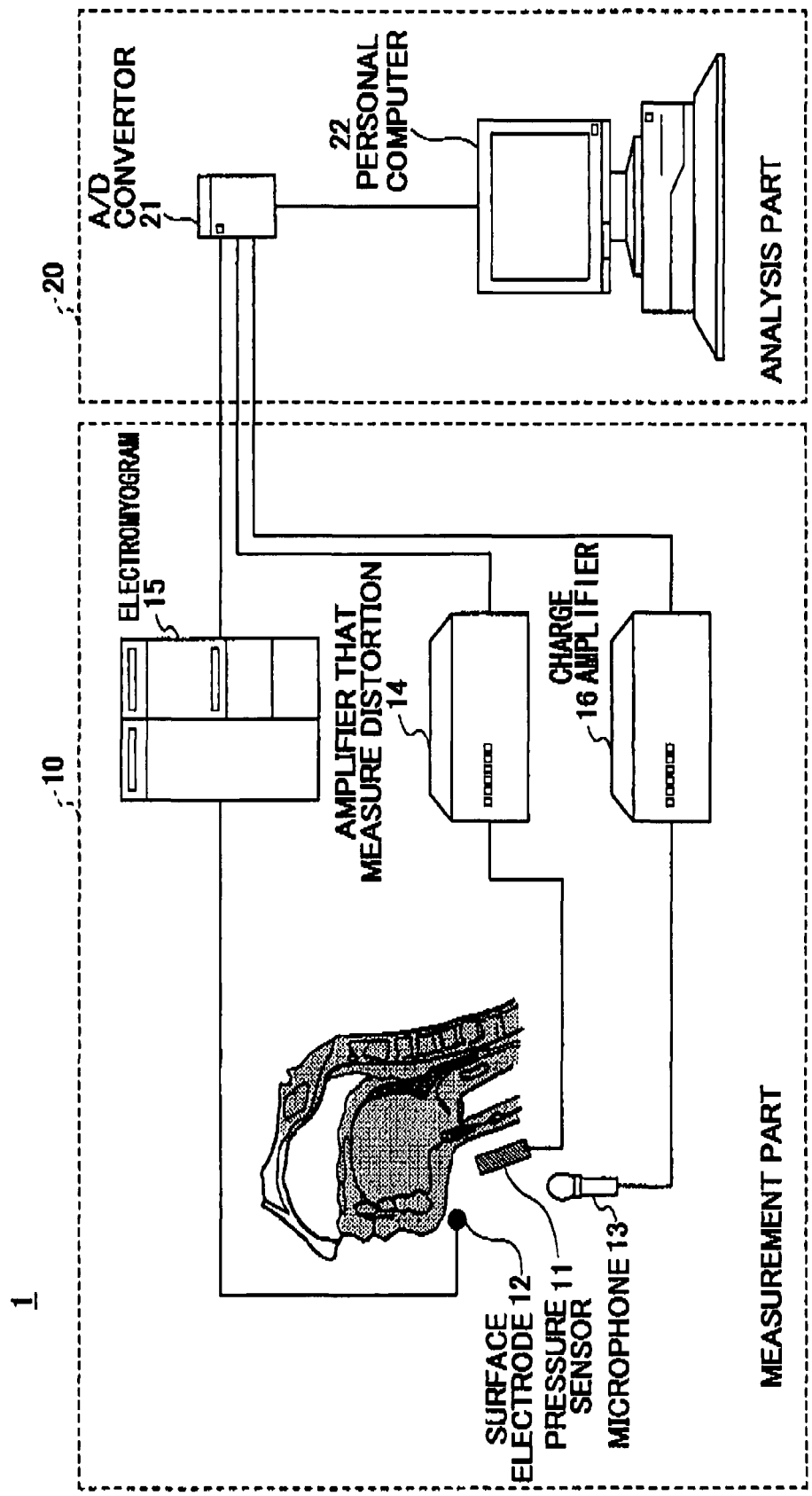
FIG. 1 is a structural view showing a conventional swallowing movement measuring device.
Figure 2:
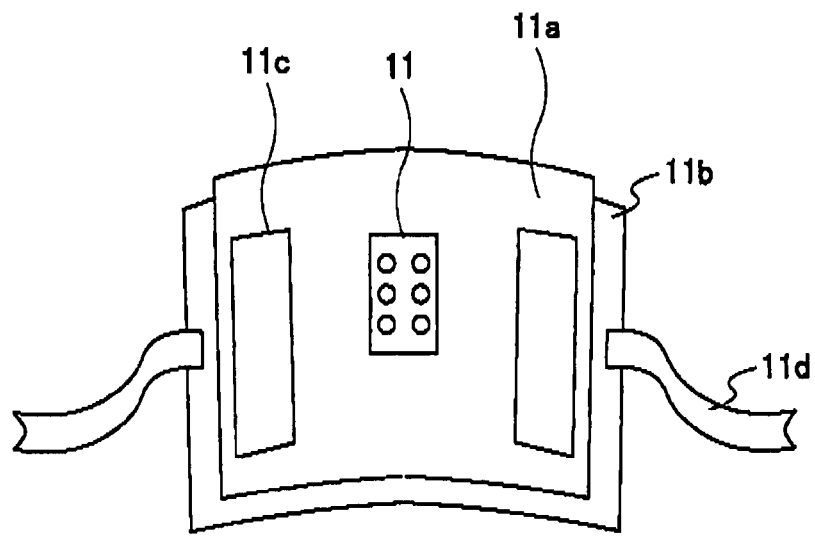
FIG. 2 is a view showing the pressure sensor.
Figure 3:
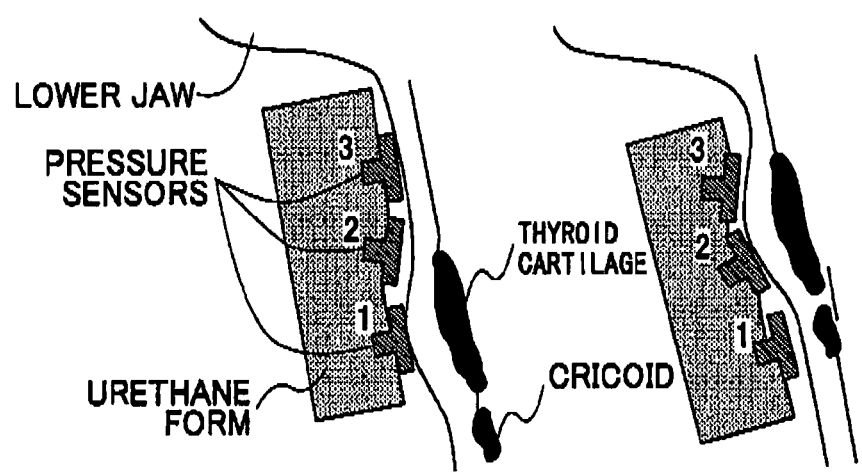
FIG. 3 is a view showing the pressure sensor attached to the anterior region of the neck and the detection principle of the swallowing movement.
Figure 4:
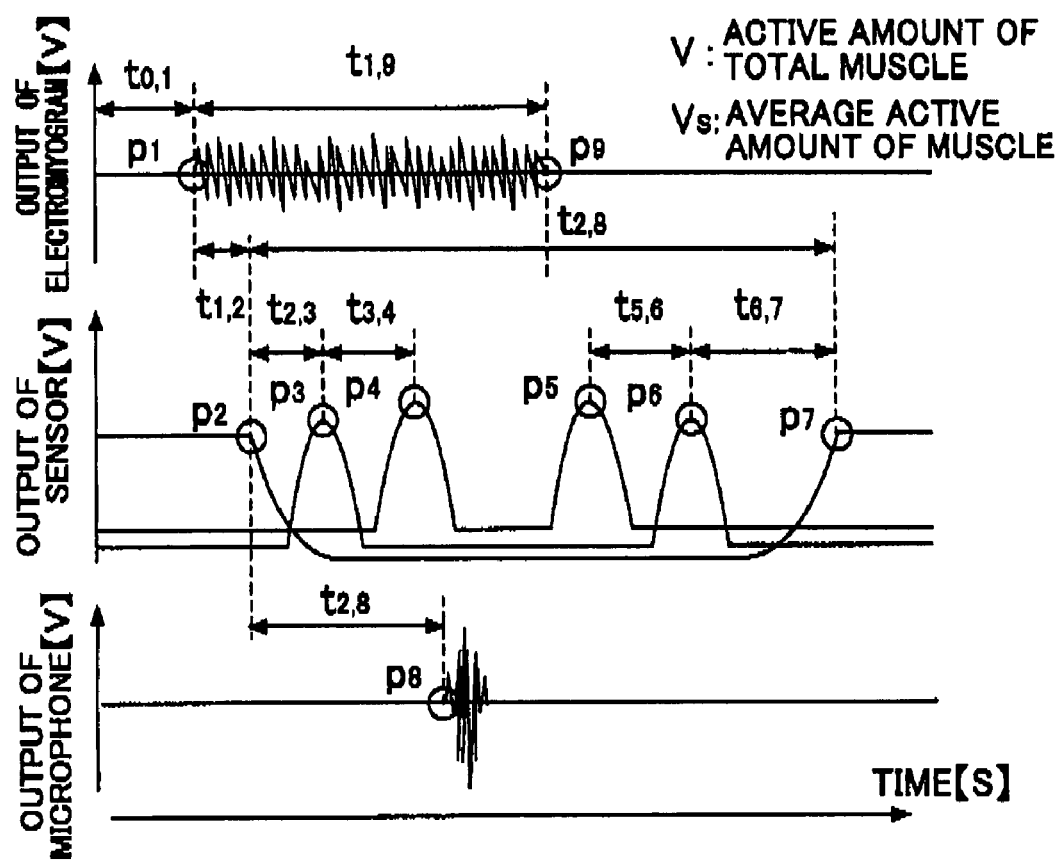
FIG. 4 is a view showing signal waves obtained from the pressure sensor, the myogenic potential electrometer electrode (the electromyogram) and the microphone.

The surface electrode of a myogenic potential electrometer 112 and the vibration pickup 113 are the same as in FIG. 1; the EMG surface electrode 112 is affixed to the equivalency region of the mylohyoid muscle of the digastric muscle, while reference electrodes (standard electrode) are attached to both earlobes. The vibration pickup 113 is attached such so as to be located beside the cricoid of the anterior region of the neck in order to measure the swallowing sound.

One difference between the swallowing movement measuring device 100 and the swallowing movement measuring device 1 is the pressure sensor 111, as described below. FIG. 6 shows a tool for wearing the pressure sensor 130 to attach the pressure sensor 111 to the cervical part. The tool for wearing the pressure sensor 130 has a sensor fixture-made of plastic 131 having a stand for the jaw 131a and a sensor mounting part 131b; urethane foam 132 is fixed at the sensor mounting part 131b, and a wearing band 134 is fixed at the sensor mounting part. Four pressure sensors s1, s2, s3 and s4 are fixed in a vertical direction at the central region of the front face of the urethane foam 132, and a both sides adhesive tape 133 is attached at both sides of the central region.

Also, the stand for the jaw 131a is supported by an axle 131c for rotating relative to the sensor mounting part 131b and can be adjusted for an angle of the plane of the stand for the jaw 131a.

The reason for this is that there are persons whose thyroid cartilage protrudes and also there are persons whose thyroid cartilage does not stand out, and the thyroid cartilage is multifarious.

Figure 7:
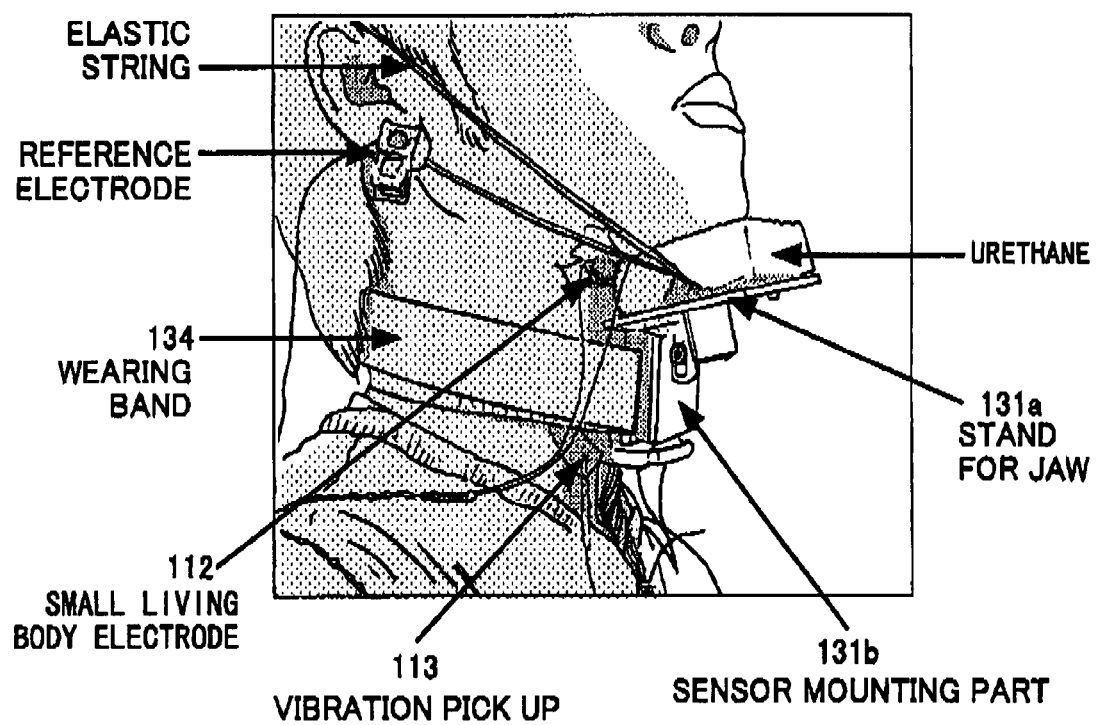
FIG. 7 is a view showing the tool for wearing the pressure sensor, the electromyogram and a vibration pickup attached to a subject.

In the case of a person whose thyroid cartilage does not stand out, the output of each sensor may not be definitely provided. In such a case, when the head is bent a little behind, and the Adam's apple is pushed out forward, where the thyroid cartilage can be clearly defined, this adjusting angle is used for keeping the continuous swallowing movement. FIG. 7 shows the attached state of the tool for wearing the pressure sensor 130, the electrode for the electromyogram 112, and the vibration pickup 113 to a subject when the swallowing movement is measured using the swallowing movement measuring device 100 according to the present invention.

As shown in FIG. 7, wearing the pressure sensor 111 at the anterior region of the neck is performed using the tool for wearing the pressure sensor 130 shown in FIG. 6, but pressure sensors s1, s2, s3 and s4 which are fixed in the urethane foam 132 are placed on the anterior region of the neck. In this case, the sensor s1 which is placed on the lowest position is placed on the thyroid cartilage and the sensor s1 is fixed at the position by both sides adhesive tape 133 of the front of the urethane foam 132. Also, the sensor s1 is fixed at the cervical part by using the wearing band 134 in this state. Then, the jaw of a subject is placed on the stand for the jaw 131a. By means of fixing like the statements above, an angle between the jaw and the neck can be fixed. When the head is moved during the measurement and the angle between the jaw and the neck changes, then the relative position between the thyroid cartilage and the pressure sensor changes, and the measurement cannot be performed.

Also, the position of the jaw is adjustable by placing the low repulsion urethane foam having appropriate depth between the jaw and the stand for jaw 131a. Also, as shown in FIG. 7, an elastic string attached to the stand for jaw 131a, an elastic string engaged with the ears, and a surface of the stand for the jaw 131a can be fixed.

The surface electrode of a myogenic potential electrometer 112 is affixed to the equivalency region of the mylohyoid muscle of the digastric muscle, and the reference electrodes (standard electrodes) are attached to both earlobes. The vibration pickup 113 is attached at the narrow part of the neck located beside the cricoid.

EXAMPLES

Figure 8:
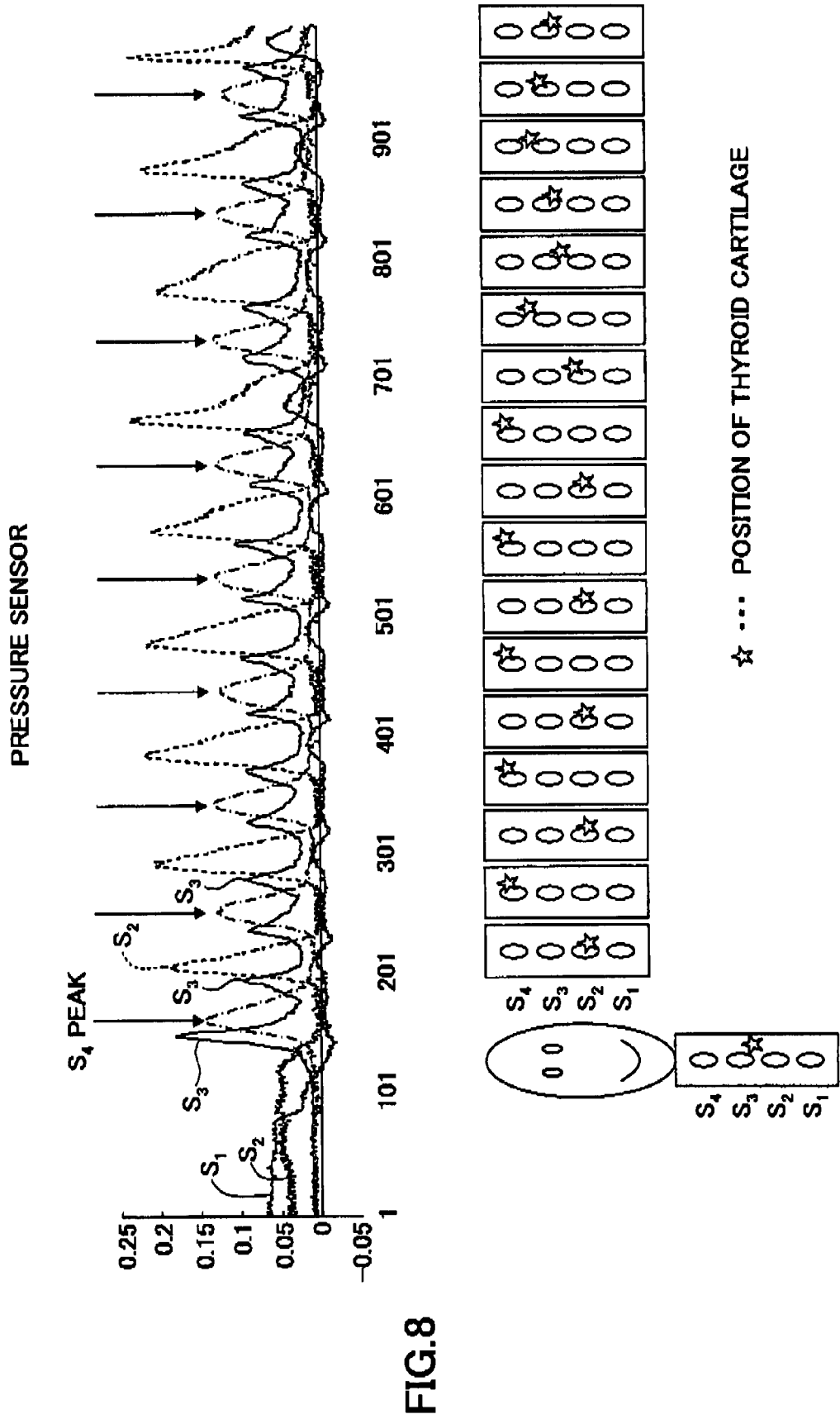
FIG. 8 is a graph showing the measurement data which are obtained by the pressure sensor.
Figure 9:
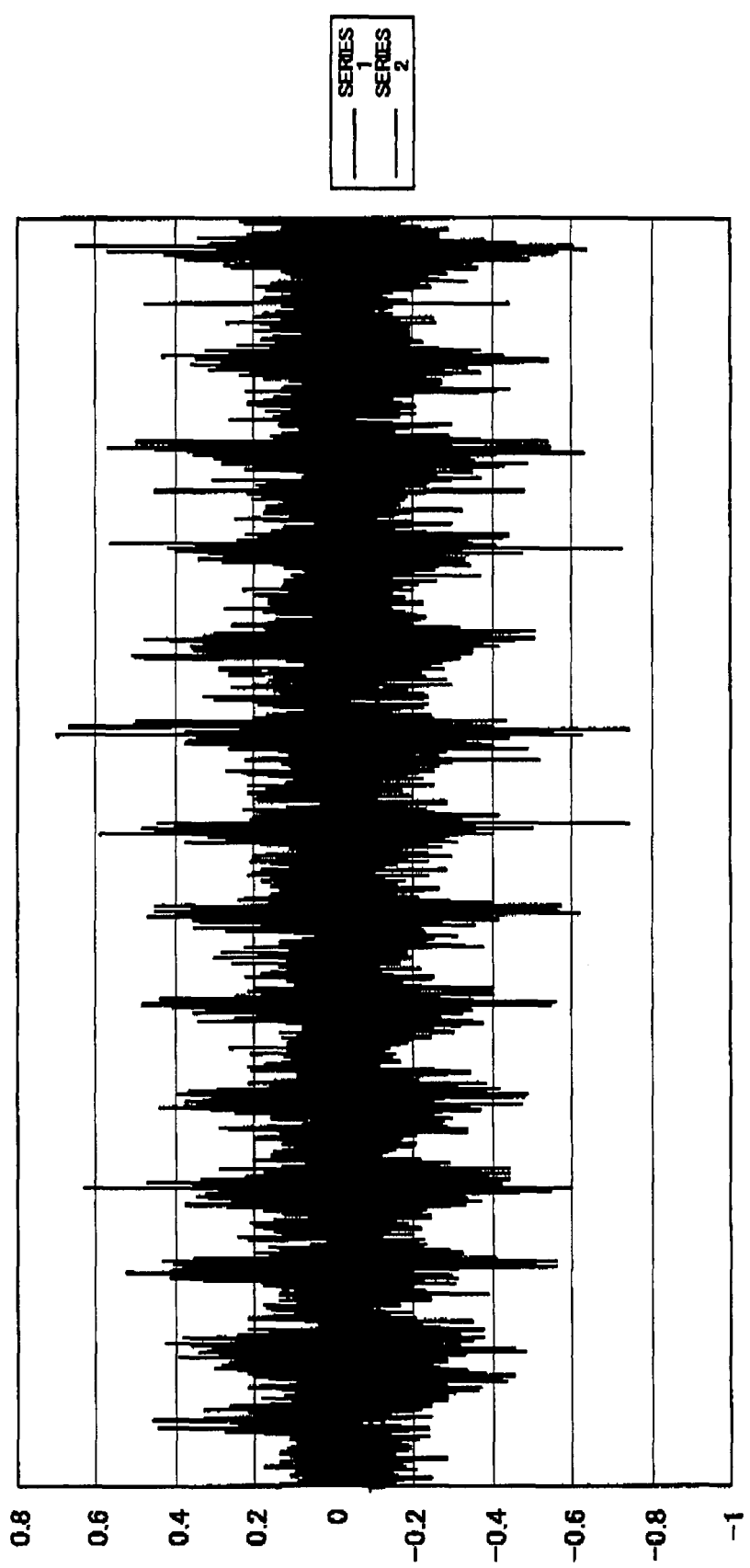
FIG. 9 is a graph showing the measurement data which are obtained by the myogenic potential electrometer.
Figure 10:
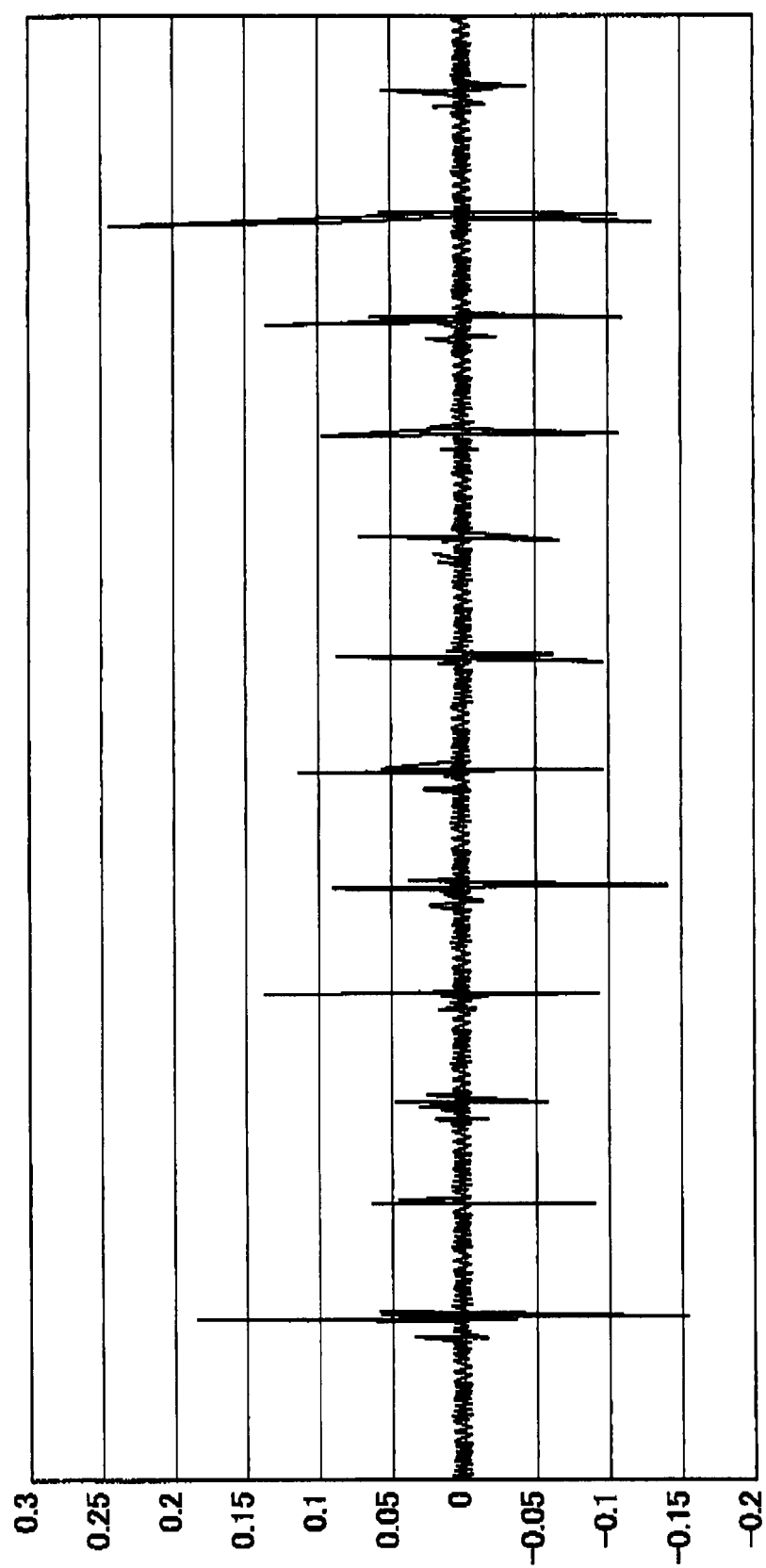
FIG. 10 is a graph showing the measurement data which are obtained by the vibration pickup.

As described above, where each sensor was fixed, a subject drank commercial natural water as samples in succession, and example measuring with the swallowing movement measurement device 100 was performed. FIGS. 8-10 show graphs of measurement data which were measured by the pressure sensor 111, the myogenic potential electrometer 112 and the vibration pickup 113, respectively. Also, the drinking time was about 10 seconds.

According to the output of the pressure sensor 111 of FIG. 8, it is recognized that changes of output of four sensors a1, s2, s3 and s4 appear periodically. FIG. 8 represents the periodic up-and-down motion that is performed with the pharynx (the thyroid cartilage) when drink is drunk continually with "glug, glug, glug, . . . ".

FIG. 9 shows an output from the myogenic potential electrometer 115, and the motion of the suprahyoid muscle group appears periodically. Also, 2 signals appear, but they are 2 signals from the myogenic potential electrometer attached on the left and the right and show peaks appearing periodically.

FIG. 10 shows output waves from the vibration pickup 113, and at the same time, the swallowing sound is detected.

Here, referring to FIG. 11 and FIG. 8, the relationship between the swallowing motion and outputs from pressure sensors s1, s2, s3 and s4 is explained.

The motion of the thyroid cartilage when a thing is swallowed is to move with the cover (the epiglottis) which does a change of the trachea and the esophagus, so that the thyroid cartilage goes up (from the trachea to the esophagus) when the thing is swallowed, then the thyroid cartilage returns to (from the esophagus to the trachea) the original position. Since the movement of the thyroid cartilage is changed where there is no bone close to the skin of the throat, the motion of the thyroid cartilage can be detected by the output of the pressure sensor 111 attached to the skin.

FIG. 11 shows outputs of pressure sensors s1, s2, s3 and s4 placed in line in the vertical direction in relation to the typical movement of the thyroid cartilage. Before starting to swallow a thing, the top position of the thyroid cartilage is placed at sensor s1 position (FIG. 11a), and the output of s1 is the highest level. At this time, since a part of the thyroid cartilage corresponds to the sensor 2, the output of s2 also occurs, and the output level of s2 is lower than that of s1. When swallowing, the thyroid cartilage rises (FIG. 11b), and output data sequentially move to the sensors s2, s3 and s4. When drinks are drunk continually with "glug, glug, glug, . . . " (continuous swallowing movement), the thyroid cartilage moves in a range of an arrow shown in FIG. 11b. In this example, at the continuous swallowing movement, the thyroid cartilage moves in a range between the sensor s2 and s4, and output peaks of each sensor appear sequentially corresponding to its movement. In addition, changes of output of the above pressure sensors s1-s4 are also different depending on the fixing relationship between the thyroid cartilage and the pressure sensors s1-s4, but there is no change of the situation in that each sensor's output peak occurs sequentially depending on the movement of the thyroid cartilage at the time of the swallowing movement.

According to the above example, it is recognized that the swallowing movement when drinking beverages continuously can be measured electrically. For the swallowing movement measuring device 100 according to the embodiment of the present invention, the pressure sensors s1-s4 are fixed on the tool for wearing the pressure sensor 130 having the above structure; thereby at the time of the continuous swallowing, the position of each sensor is not moved and changes of signals can be measured accurately. Therefore, the swallowing movement can be measured accurately.

Next, using the above continuous swallowing movement measuring device 100, the thyroid cartilage, the active amount of the suprahyoid muscle group, and the swallowing sound when drinking beverages continuously are measured, then the measurement results are considered.

Generally, in the case of drinking a beverage, for example, the beverage is water, juice or beer, etc., everybody feels that there are differences for feelings at the throat at the time of swallowing the drink and the easiness to swallow food depending on various types of beverages, but methods to evaluate the above feeling and easiness objectively have not yet been established. Inventors of the present invention considered the objective evaluation of feelings at the throat at the time of swallowing a drink, the easiness to swallow food and the drinkability by using the above swallowing movement measuring device 100.

First of all, natural water, juice and beer were selected as samples for beverages. Then, plural subjects (10 people) drank these beverages continuously, and measurement data of time periods of up and down motion of the thyroid cartilage, the active amount of the suprahyoid muscle group, and the time periods of the swallowing sound were obtained. The results were analyzed by using the swallowing movement measuring device 100 of the present invention.

Figure 12:
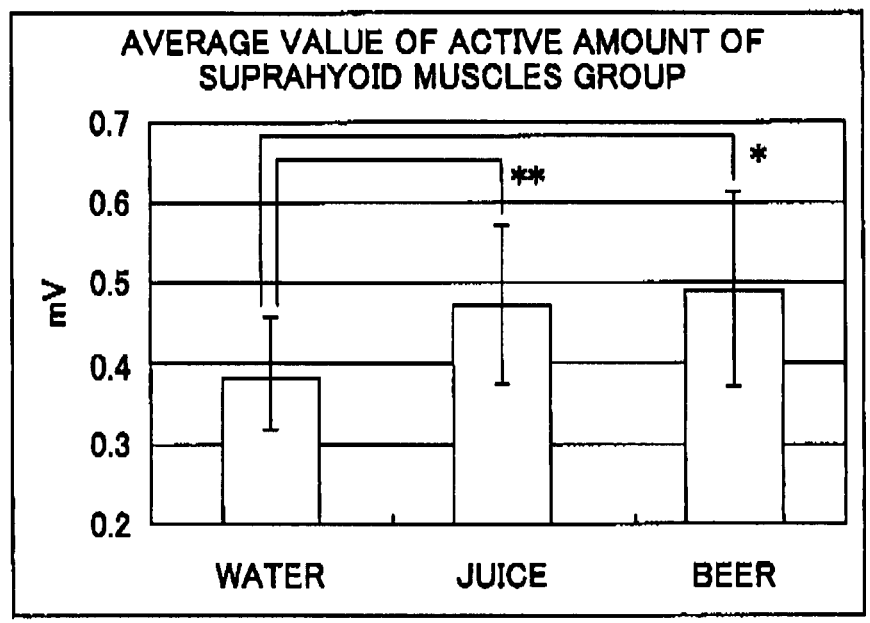
FIG. 12 is a graph showing a relationship between the a kinetic amount of the suprahyoid muscle group and beverage type.

First of all, a force of muscle (active amount of the suprahyoid muscle group) when beer is being drunk can be recognized based on a measurement value of the myogenic potential electrometer. FIG. 12 represents the average value of the muscle's active amount of 10 subjects for each beverage. It is recognized that the average value of the muscle's active amount of water is smaller than that of juice and beer and there is a significant difference between water and juice, also between water and beer based on the graph of FIG. 12. That is, more force is applied by the muscle at the time of drinking juice or beer rather than at the time of drinking water with "glug, glug, glug, . . . ".

The small amount of the muscle's active amount means easiness to drink, and from this point of view, it is recognized that beer and juice are hard to drink compared to the drinking water. On the other hand, since this hardness to drink shows active movement of the suprahyoid muscle group, it might be one of the elements when an index of "light finish sensation in the throat" and "full finish sensation in the throat" is established.

Figure 13:
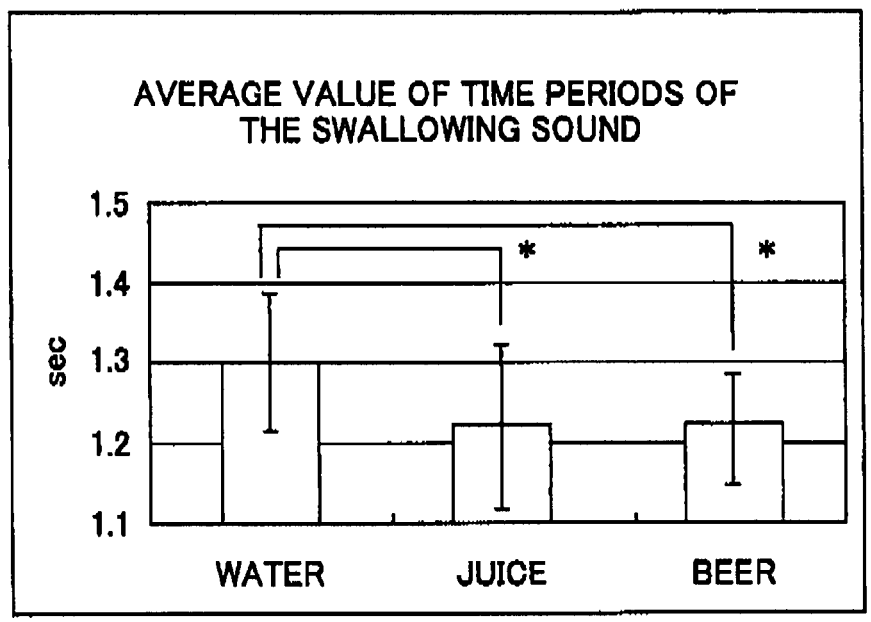
FIG. 13 is a graph showing a relationship between time periods of swallowing sound and beverage.

Next, FIG. 13 shows the results of average values of time periods of the swallowing sound (periods for which peaks appear in FIG. 10) obtained from the vibration pickup 113. It is recognized that there are significant differences between water and juice, also between water and beer. It is recognized that time periods of the swallowing sound are short at the time of drinking juice and beer rather than at the time of drinking water with "glug, glug, glug, . . . ". That is, it was suggested that is more gurgling sound with "glug, glug, glug, . . . " from the throat at the time of drinking juice and beer rather than at the time of drinking water.

The sound of "Gurgle" ("glug, glug, glug, . . . ") that frequently occurs at the time of continuously drinking a beverage is the same feeling as senses such as the feeling at the throat at the time of swallowing a drink, so that it might provide possible data representing the feeling at the throat at the time of swallowing a drink of beer.

Figure 14:
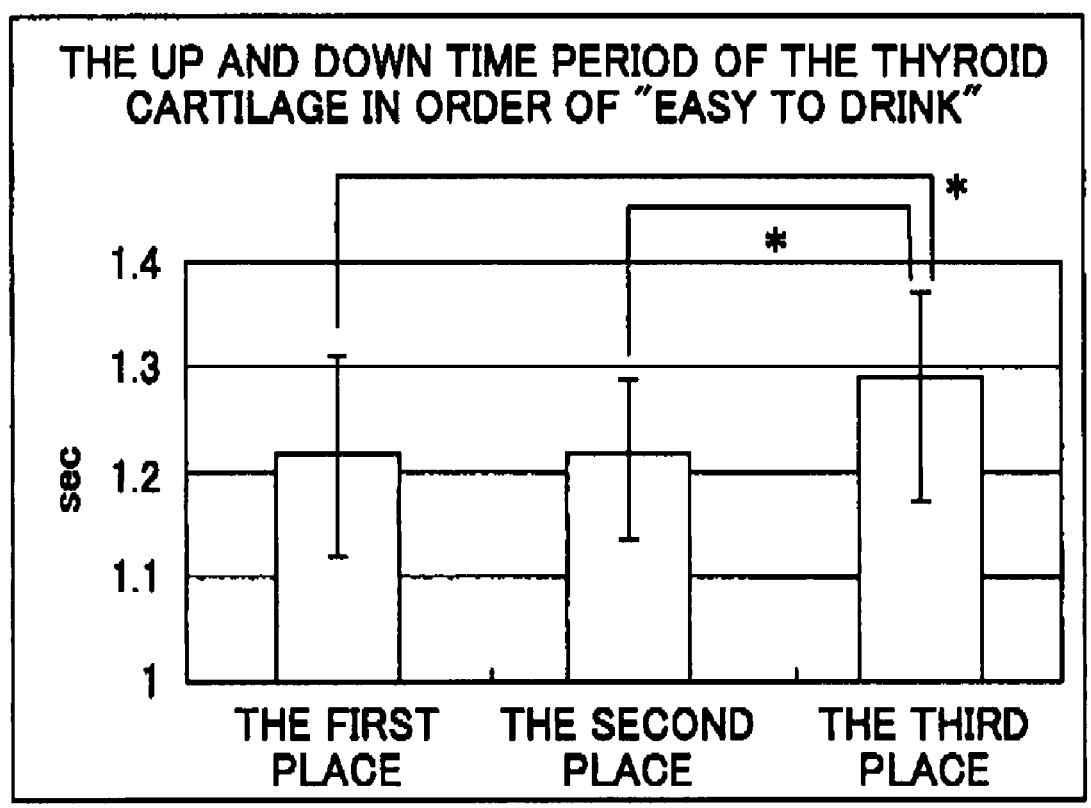
FIG. 14 is a graph showing a relationship between the vertical motion of a thyroid cartilage and beverage.

FIG. 14 is a result showing a relationship between the up and down time period of the thyroid cartilage obtained based on the measurement data from the pressure sensor 111 and beverage type. Here, an evaluation of sense for being easy to drink was performed for 10 people of subjects concerning water, juice and beer (ordering for easiness to drink), and it shows a relationship between its order and the up and down time period of the thyroid cartilage.

For the ordering of the evaluation of sense, the first place was water, the second place was juice and the third place was beer. Comparing easy to drink and the up and down time period of the thyroid cartilage of the evaluation of sense, the longest period of the up and down time period of the thyroid cartilage was for beer, evaluated to be in third place, and it is recognized that for beer there is a significant difference from samples of the first place and the second place. Therefore, the up and down time period of the thyroid cartilage might be one possible element when an index of "easiness to drink" for beverages is established.

As described above, by using the continuous swallowing movement measuring device 100 of the present example, the thyroid cartilage movement, the movement of the suprahyoid muscle group, and the swallowing sound at the time of continuously drinking beverages can be measured accurately. Also, applying these measured data to the evaluation and diagnosis of the swallowing movement of the subject can contribute to a diagnosis of the ability for swallowing of the subject, and evaluation and development of food and drink.

The above example is the study of an active movement of the suprahyoid muscle group, time periods of the swallowing sound, and the up and down time periods of the thyroid cartilage for samples of beverages selected as natural water, juice and beer. Next, as a sample of beverage, the example that a kind of alcoholic beverage having foaming properties is changed was performed and its result is explained. As the alcoholic beverage having foaming properties, beer A (beverage A), beer B (beverage B) and beer like an alcoholic beverage (beverage C) were selected as samples. First of all, characteristics of each sample were determined by sense examination.

Figure 15A:
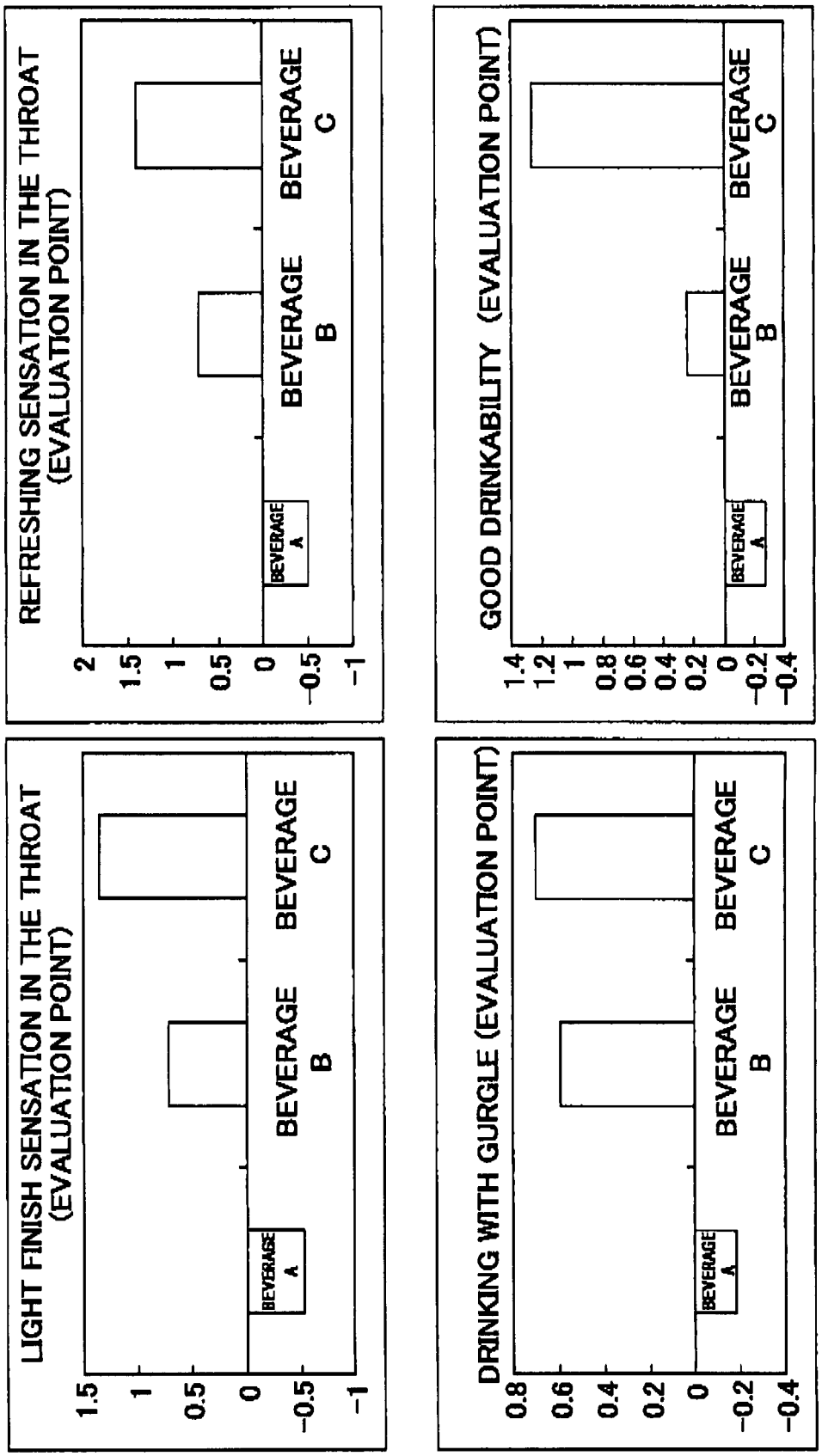
FIG. 15A is a graph showing a sense examination result of alcoholic beverage with foaming properties.
Figure 15B:
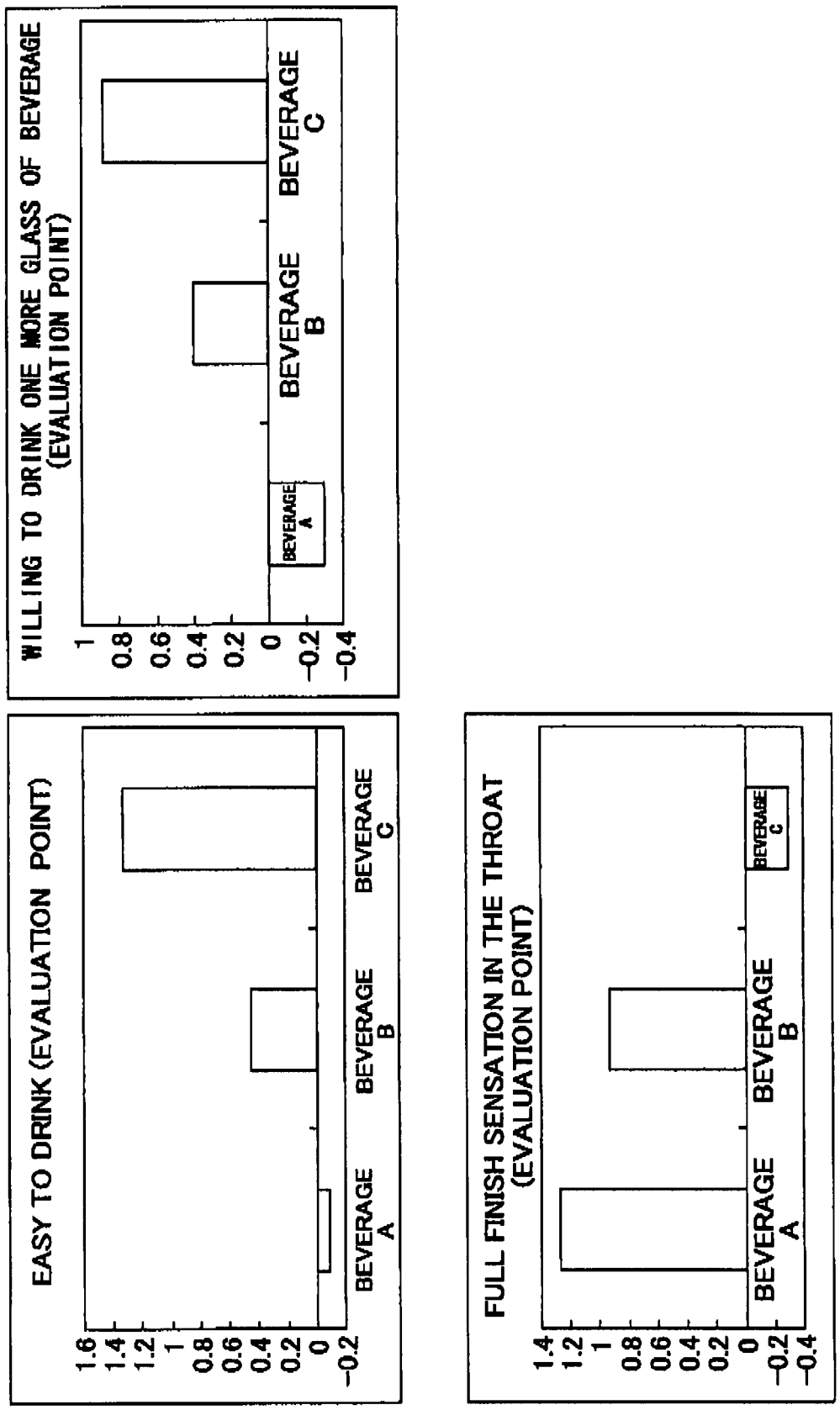
FIG. 15B is a graph showing a sense examination result of alcoholic beverage with foaming properties.

In FIGS. 15A and 15B, results of sense evaluation of 10 people as subjects about beverages A, B and C are shown. In FIG. 15A, "light finish sensation in the throat", "refreshing sensation in the throat", "drinking with gurgle" and "good drinkability" were evaluated for respective beverages by each subject, and points were added and evaluated from −2 points to +2 points as the evaluation method. Also, FIG. 15B shows results evaluated the same as in the above evaluation method about "easy to drink", "willing to drink one more glass of beverage" and "full finish sensation in the throat".

According to results of sense examinations of FIGS. 15A and 15B, characteristics of each beverage are as follows.

About the Beverage A:

Evaluations of "light finish sensation in the throat", "refreshing sensation in the throat", "drinking with gurgle" and "easy to drink" were negative according to results of sense examinations. On the other hand, about "full finish sensation in the throat", it was the highest evaluation among the samples. That is, it is recognized that the beverage A is mellow and a richness type in alcoholic beverages having foaming properties.

About the Beverage B:

Among the three samples, the evaluations about being easy to drink like "easy to drink", "light finish sensation in the throat", "refreshing sensation in the throat", "drinking with gurgle", etc., are higher than those of the beverage A. However, the evaluation about "full finish sensation in the throat" is inferior to that of the beverage A, but is definitely superior to that of the beverage C. That is, it is clear that the beverage B has a characteristic which opposing evaluations of "easy to drink" and "full finish sensation in the throat" are moderately balanced.

About the Beverage C:

Among three samples, the evaluations about being easy to drink like "easy to drink", "light finish sensation in the throat", "refreshing sensation in the throat", "drinking with gurgle" and "willing to drink one more glass of beverage" are the highest of the three samples. On the other hand, the evaluation about "full finish sensation in the throat" is inferior to those of beverages A and B. Based on these, it was clear that this sample is an alcoholic beverage having foaming properties which has a characteristic of easy to drink for smooth and highly refreshing drinkability.

Next, about each sample having different characteristics as described above, the muscle's active movement of the suprahyoid muscle group, time periods of the swallowing sound and the up and down time period of thyroid cartilage for 10 people as subjects who participated in sense examinations were studied.

FIG. 16 is a graph showing average values of the kinetic amount of the suprahyoid muscle group about each beverage A, B and C. According to the graph, when placing in order the active amount of the muscle of the throat at the time of drinking, the largest was the beverage A, the second largest was the beverage B and the last was the beverage C. The large kinetic amount of the suprahyoid muscle group predicts a relationship with "full finish sensation in the throat" or in reverse "easy to drink" of items of the above sense examination, so that it is recognized that the evaluation of "full finish sensation in the throat" of the beverage A, the evaluation of "easy to drink" of the beverage C and the kinetic amount of the suprahyoid muscle group have a relationship, and the relationship is very interesting.

The FIG. 17 shows a graph which examined average values of time periods of the swallowing sound obtained from the vibration pickup. As explained in FIG. 13, about time periods of the swallowing sound, when the time period of the swallowing sound is short, it is shown that beverage flows down the throat smoothly at the time of drinking and it is predicted "easy to drink". According to the data of measurement, there is no big difference among the data of beverages A, B and C, but the data of "full finish sensation in the throat" beverage A has the largest value. It is predicted that there is relevance with the data of the minimum value of the beverage C which is evaluated as the easiest to drink in the above sense examination.

Figure 18:
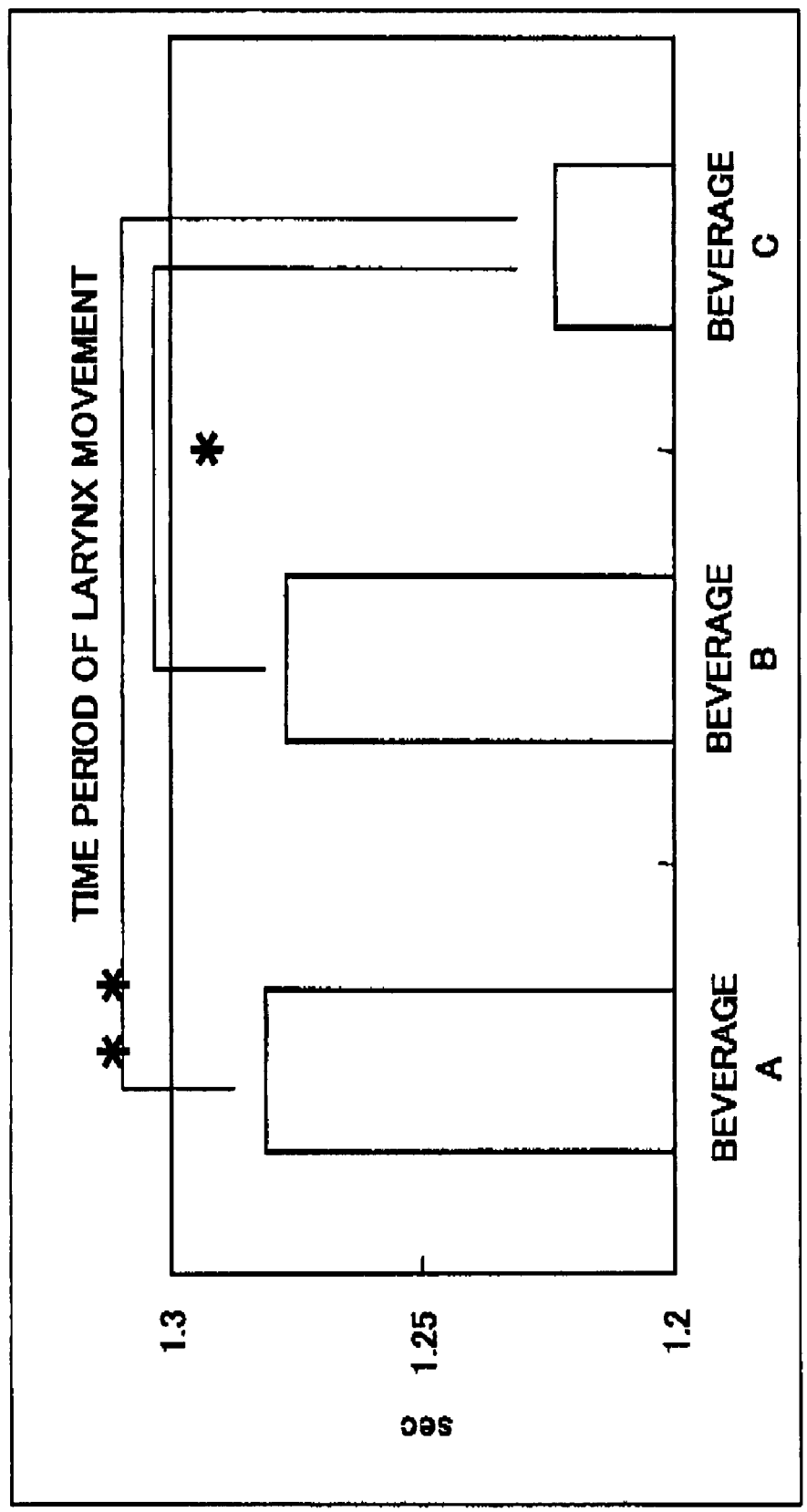
FIG. 18 is a graph showing a relationship between the vertical motion of the thyroid cartilage and alcoholic beverage with foaming properties.

FIG. 18 shows a result of examining the up and down time period of the thyroid cartilage obtained from the data of measurement of the pressure sensor 111. As shown in the graph, the period of the beverage C (beer-like alcoholic beverage) has the shortest period and the beverage A has the largest value; also the difference between the data of the beverage A and the data of the beverage B was small. It is predicted that the data of FIG. 18 can evaluate the smooth movement of the Adam's apple; it can be considered that the beverage flows down the throat smoothly when the time period is short. According to the result of the above sense examinations, the period of "full finish sensation in the throat" beverage A (beer) has the longest period, and the relevance with the data which period of the beverage C evaluated as "easy to drink" has the shortest period is very interesting.

As described above, conventionally, the evaluation method for beverages sensuously with "full finish sensation in the throat", "drinkability", "easy to drink", etc., for beverages may become one of the indexes to express as data with numerical values objectively. Also, it may be used as an index of development of beverages and a quality indication of beverages. Also, the continuous swallowing movement measuring device of the above embodiment is explained about the example where the movement of the Adam's apple at the time of swallowing movement was picked up using plural pressure sensors. Next, the second example that the movement of the Adam's apple that swallowing movement is measured by using the small reflection type optical sensor that is a non-contact sensor instead of using pressure sensors is described below.

Figure 19:
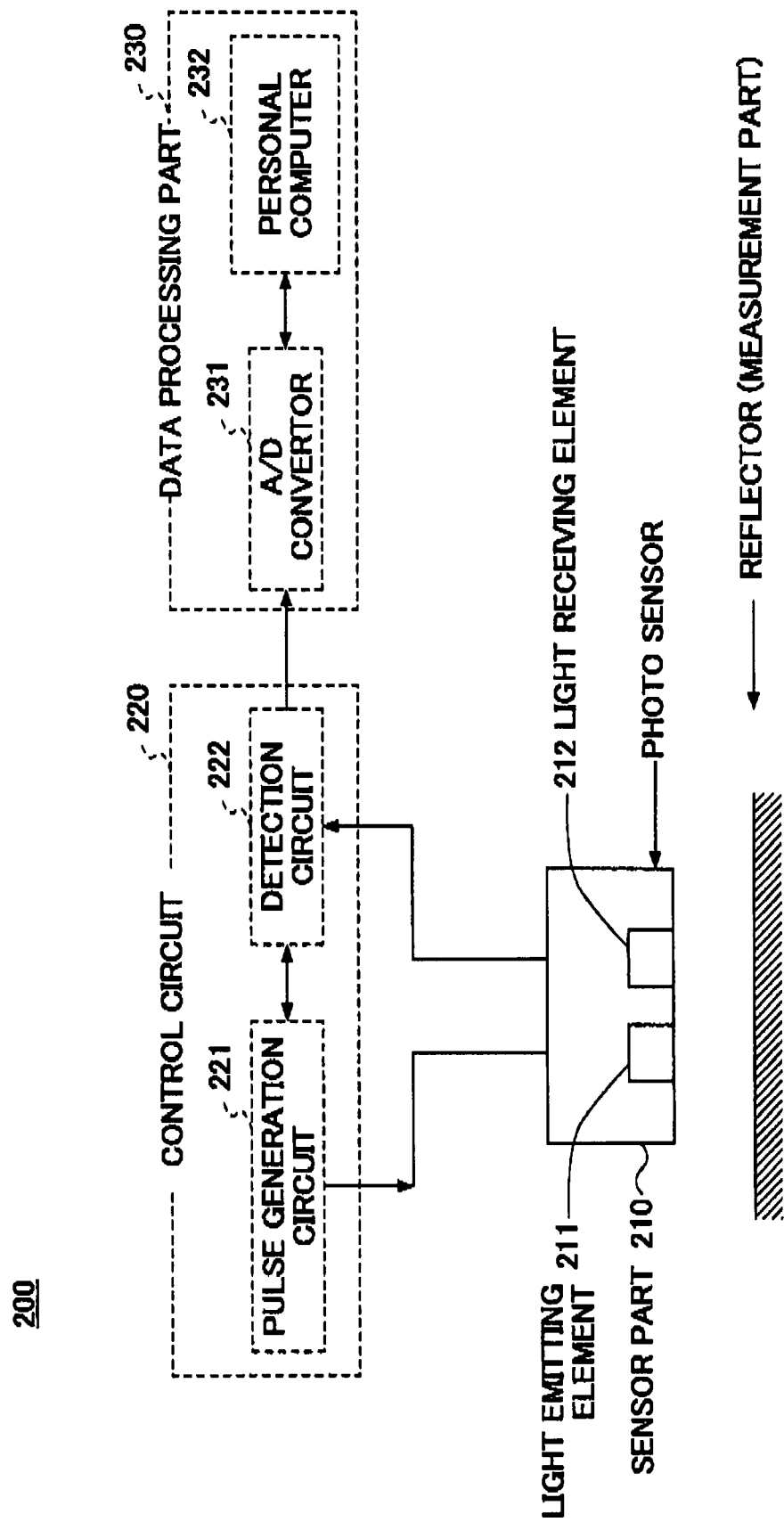
FIG. 19 is a view showing the swallowing movement measuring device with the reflection type optical sensor of the embodiment of the present invention.

First of all, according to FIG. 19, the swallowing movement measuring system 200 with the reflection type optical sensor of the present embodiment is explained.

The swallowing movement measuring system 200 is composed of a sensor part 210 comprising the reflection type optical sensor, a control circuit 220 and a data processing part 230. As described below, the system is such that a light is emitted from the optical sensor depending on an output pulse from a pulse generation circuit of the control circuit; the light reflected back with a reflector is detected in a light-receiving section of the optical sensor; the intensity of the light is detected by a voltage detection circuit and it is amplified, then it is input in a personal computer through an A/D converter; and distance from a sensor reflector is calculated based on the detection voltage, then it is displayed and analyzed.

The sensor part 210 has a light emitting element 211 and a light receiving element 212, and the sensor part 210 is constructed such that the light emitted by the light emitting element 211 is irradiated in a measurement part, and the light reflected back by the measurement part is received in the light receiving element 212. Also, an infrared light emitting diode (LED) is used as the light emitting element 211 in the present example.

The control circuit 220 has the pulse generation circuit 221 and the detection circuit 222. The pulse generation circuit 221 is such that a rectangular wave is generated at a non-stable multi-vibrator, a period pulse having a period of 10 ms and a width of 0.1 ms is generated by inputting the rectangular wave in a single stable multi-vibrator, and a mirror constant electric current circuit is driven by this pulse so that the light emitting element (LED) 211 emits light.

The detection circuit 222 comprises the voltage detection circuit detecting the output voltage of the light receiving element (photo transistor) 212, and the detection circuit 222 consists of a sample holding circuit, a low pass filter (LPF) removing noise and a non-tuning amplification circuit which amplifies the detection voltage.

The sample holding circuit samples the photo transistor output when the drive pulse is 1 and holds the photo transistor output when the drive pulse is 0. From the signal, sample pal and noise are removed by means of the primary LPF. In this case, the cutoff frequency was 140 Hz.

The data processing part 230 has the A/D converter 231 and the personal computer 232.

The output voltage detected at the detection circuit is transferred to the data processing part 230, then it is transferred to the personal computer 232 via the A/D converter 231 and processed there.

Figure 20:
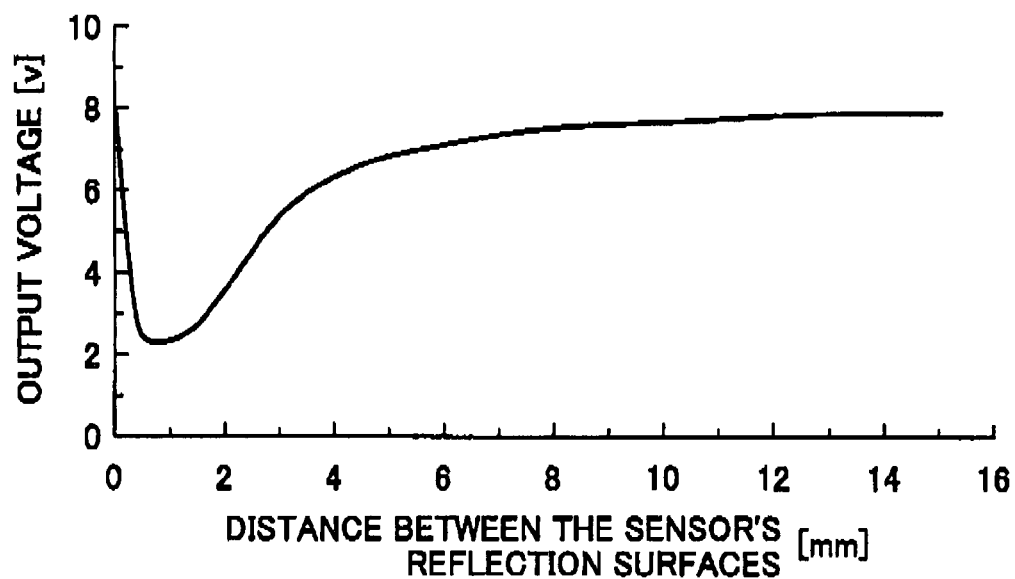
FIG. 20 is a graph explaining a characteristic of the reflection type optical sensor.
Figure 21:
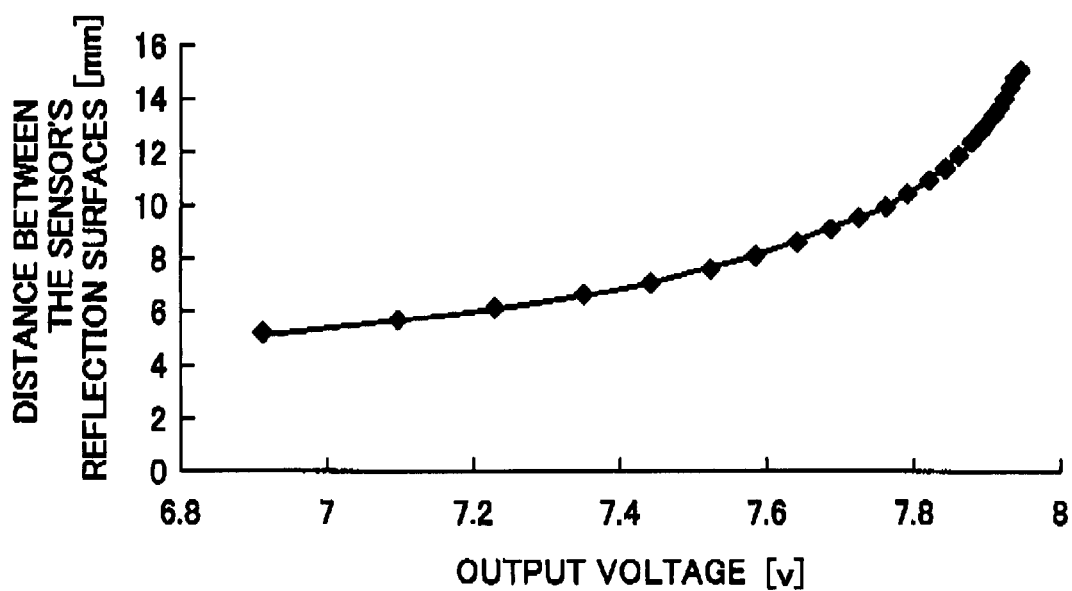
FIG. 21 is a graph showing a characteristic approximation curve of the reflection type optical sensor.

FIGS. 20 and 21 show examination results of characteristics of the reflection type optical sensor 210 used in the present example. When changing the sensor, a reflection surface and a distance, FIG. 20 shows a graph indicating a relationship between the distance and an output voltage of the sensor. As shown in the graph, the output voltage is dramatically decreased at the first stage as the distance increases, but after that, the output voltage is increased. The output was minimum around 1 mm distance.

Based on the above characteristic of the output voltage, it is recognized that it is appropriate to utilize a characteristic which is suitable for measuring a distance between the sensor's reflection surface, that is, a characteristic of the output voltage when the distance of the sensor's reflection surface is under 1 mm, or a characteristic of the output voltage when the distance of the sensor's reflection surface is between 5 mm and 15 mm. In the case of the measurement of the present invention, the optical sensor is attached at the anterior region of the neck and the swallowing movement is measured without contact, as described below. Considering the height of the thyroid cartilage, it is recognized that it is impossible to use the above characteristic of the output voltage for the measurement of the present invention.

Therefore, in the case of the present example, the distance between the sensor and the thyroid cartilage was set as about 5 mm at minimum; then a stable part of the characteristic of the output voltage of FIG. 20, in which the distance to the sensor's reflection surface is between 5 mm and 15 mm is used. In this range, a characteristic of the output voltage of the part for which the distance of the sensor's reflection surface is between 5 mm and 15 mm is shown in FIG. 21. FIG. 21 shows a characteristic curve in which the horizontal axis indicates the output voltage and the vertical axis indicates the distance to the sensor's reflection surface.

Next, the swallowing movement measuring device attaching the above optical sensor to a human laryngeal for measuring is described.

Figure 22:
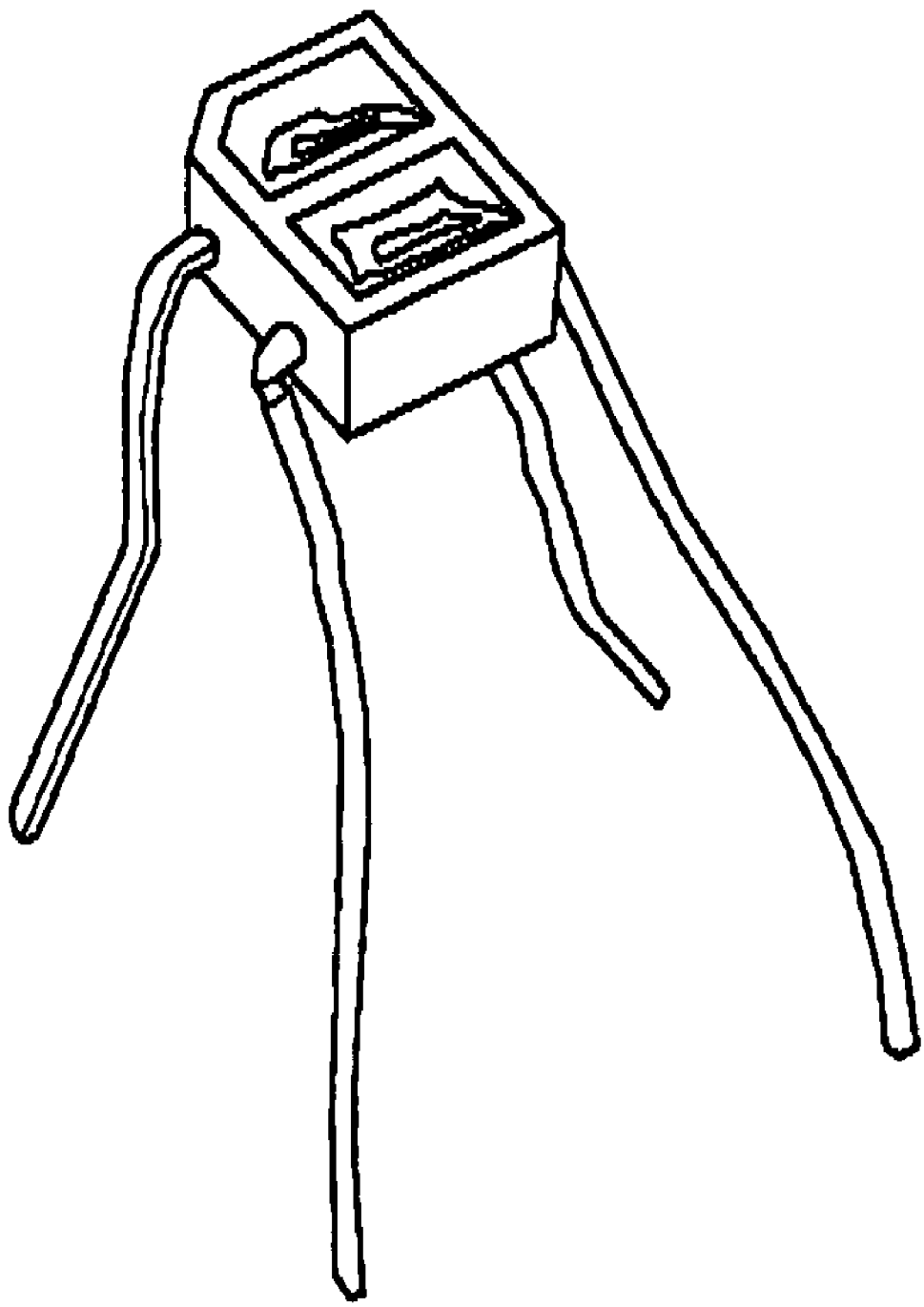
FIG. 22 is an external view of the reflection type optical sensor.

FIG. 22 is a view showing the reflection type optical sensor used in the present example, and the reflection type optical sensor has lines connected to the light emitting element and the light receiving element.

Figure 23:
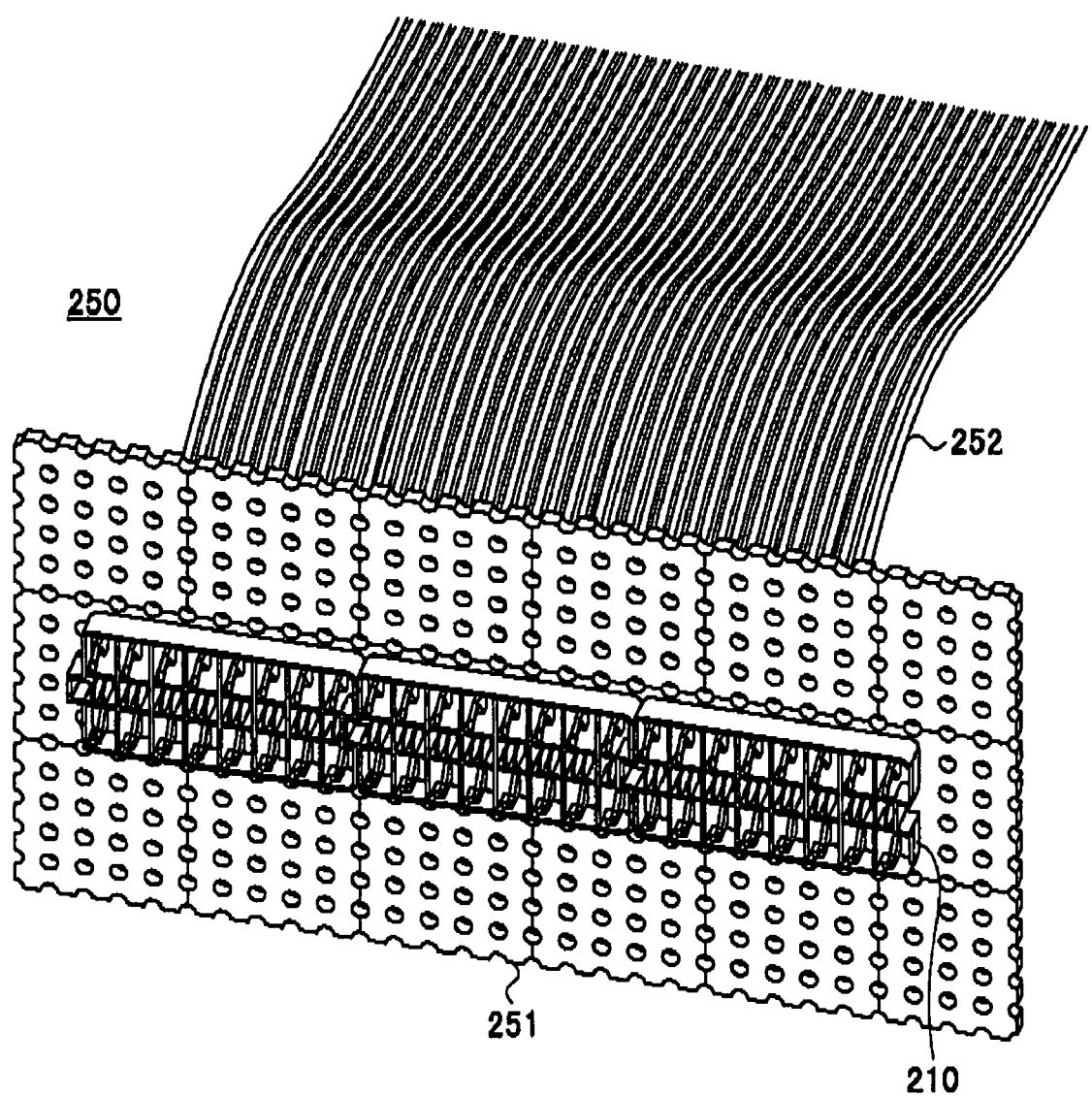
FIG. 23 is a view showing the reflection type optical sensor attached to the sensor fixation board.

FIG. 23 shows the sensor fixation board 251 of the optical sensor mounting device 250 for wearing the optical sensor shown in FIG. 22 on the anterior region of neck.

FIG. 24 shows whole view of the optical sensor mounting device 250. The optical sensor mounting device 250 comprises the sensor fixation board 251; the reflection type optical sensor 210 which is placed in a line and mounted on the board, and band 252 for fixing the sensor fixation board 251 on the anterior region of the neck. As for the sensor fixation board 251, a hard thing without a bend is used. Flexible plastic pads 253 are attached on both sides of the optical sensor 210 on the sensor fixation board 251. When the optical sensor mounting device 250 is mounted on the laryngeal, these pads 253 are such that the optical sensor 210 is held at a uniform distance from the surface of the laryngeal, that is, the optical sensor does not contact the laryngeal and also the optical sensor 210 is stably attached to the laryngeal. Moreover, urethane foam pads for shading 254 are fixed along the line of the optical sensors on pads 253 thereby so that the approach of light to the optical sensor 251 is prevented.

In the present example, 12 sensors are used for the optical sensor 210. As explained in FIG. 19, lines from the control circuit 220 are connected to each optical sensor 210; thereby the output voltage obtained from the light receiving element 212 by receiving the light is transferred to the data processing part.

Figure 25:
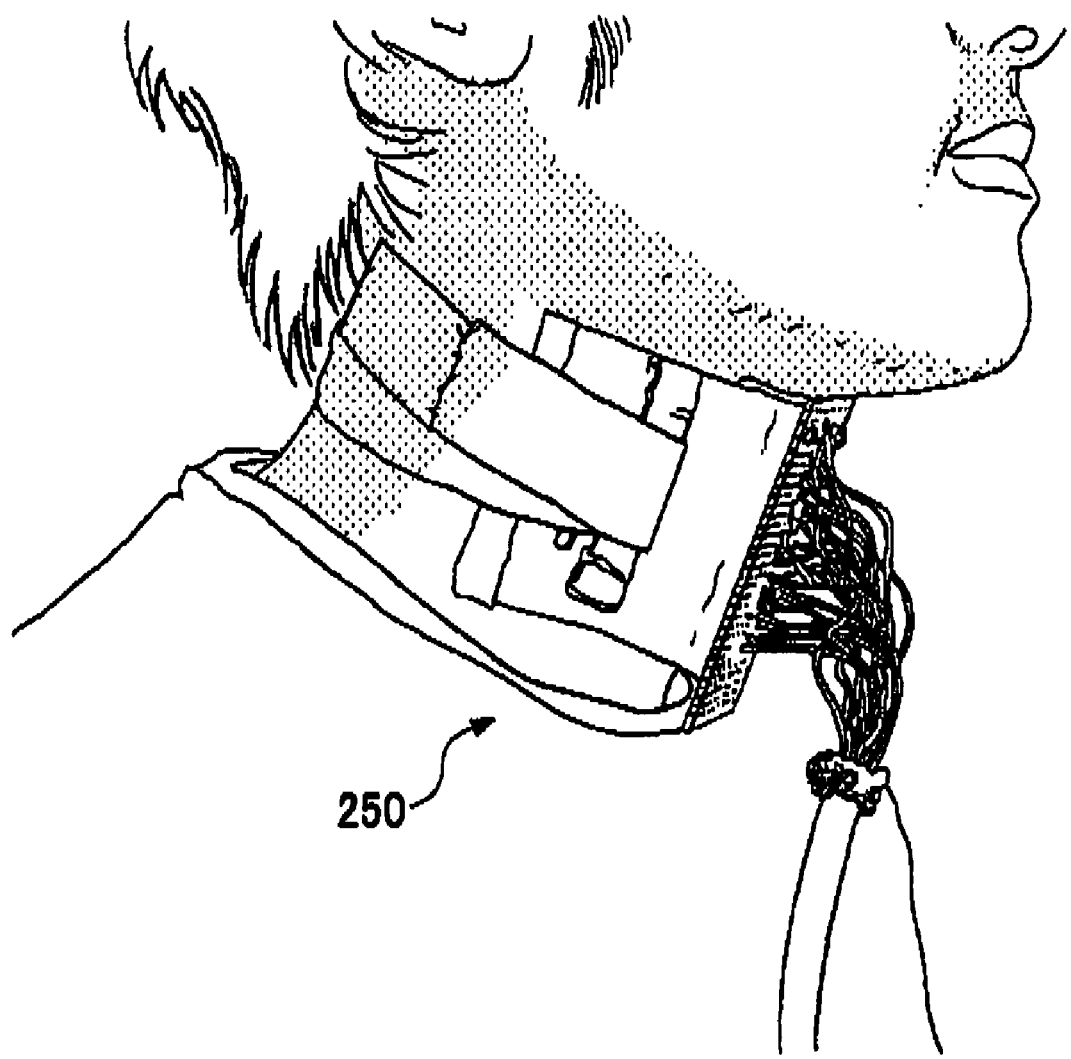
FIG. 25 is a figure showing the optical sensor mounting device attached to a subject.
Figure 26:
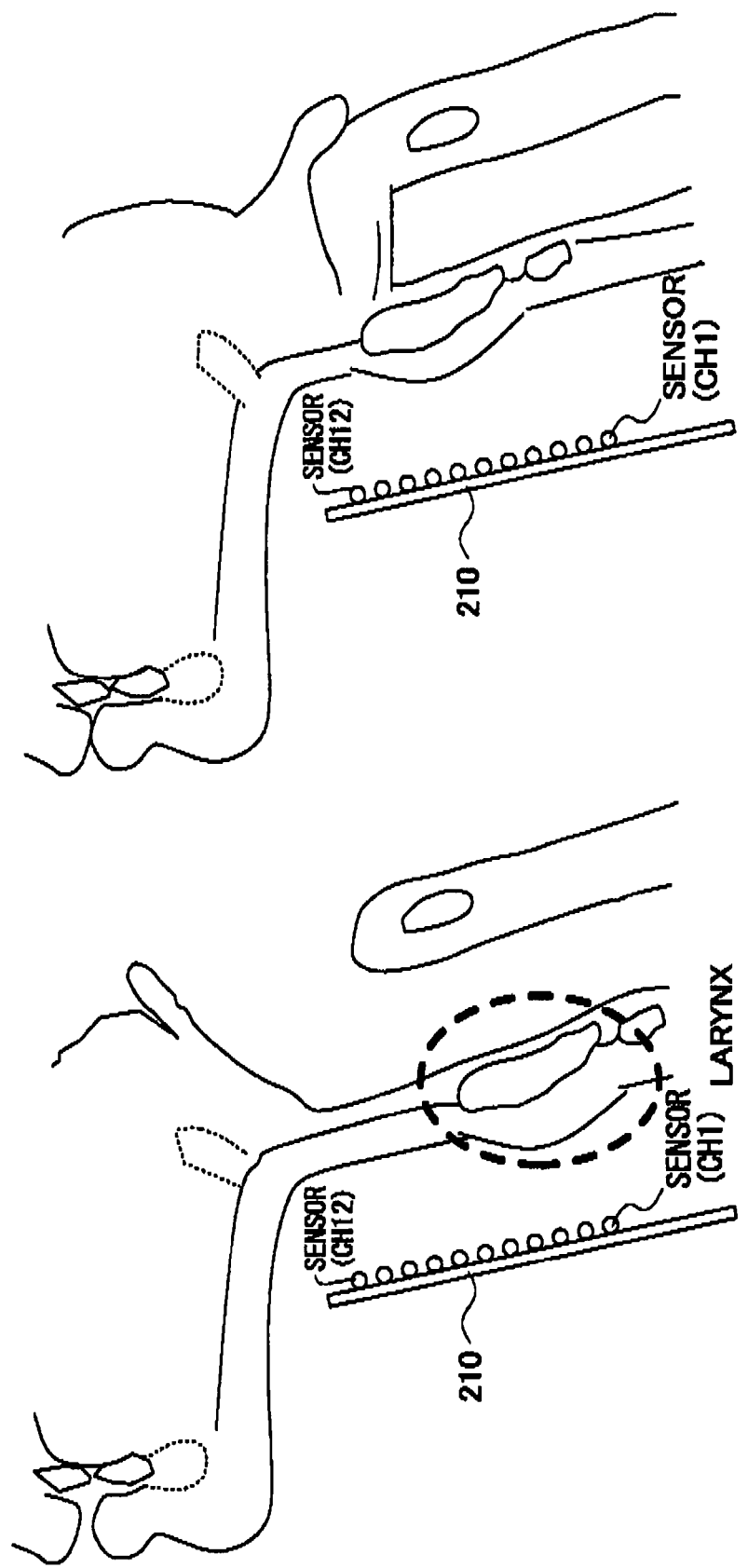
FIG. 26 is a view showing the positional relationship between the larynx and the sensor when the optical sensor mounting device is attached.

FIG. 25 shows the optical sensor mounting device 250 shown in FIG. 24 actually attached on the anterior region of the neck of a subject. Also, when the optical sensor mounting device 250 is attached to the laryngeal, as shown in FIG. 26, the optical sensor 210 is placed as a line on the position of the laryngeal, so that the lowest optical sensor among 12 sensors is placed in the neighborhood of the laryngeal. In this case, the same as the above, the distance between the optical sensor and the thyroid cartilage is the usual distance, which is 5 mm.

Next, the same as the example explained earlier, a subject drank beverages in succession with "glug, glug, glug, . . . and an output value of each optical sensor was observed. FIG. 26(a) shows a position of the larynx before the swallowing movement, and FIG. 26(b) shows the position of the larynx after the swallowing movement.

FIG. 27 shows a change of the output of 12 optical sensors at the time of drinking the beverages in succession by the progress of time (a)-(b). In FIG. 27, (a) shows the status before the swallowing and at an arrow position, the distance between the sensor and the surface of the reflector (that is the anterior region of neck) is the shortest, thereby it indicates that the larynx is positioned at this part.

Next, (b) shows the status after starting the swallowing movement; the position where the sensor and the larynx came closest is moved to an arrow position. That is, it is recognized that the larynx moved above while swallowing occurred. In addition, (a) shows the status after starting the swallowing movement; the larynx is placed at the highest position. Also, changes between (b) and (c) of FIG. 27 are repeatedly observed at the time of drinking the beverages in succession.

According to the above result, by using the swallowing movement measuring device 200 with the reflection type optical sensor of the present example, the same as using the swallowing movement measuring device 100 with the above pressure sensor, it is possible that the performance or evaluation of the swallowing movement of a subject can be examined.

In the present example, by indirectly measuring the swallowing movement using optical sensors, using pressure and wearing the cervical part of the measuring device disappear, and the swallowing movement can be measured in a more natural environment. Moreover, since each sensor is fixed on the fixation board so that the sensors do not contact the laryngeal and the sensors themselves do not move with the swallowing movement, the position of sensors is stable and measurement with high accuracy can be achieved.

In addition, the swallowing movement measuring device with the above optical sensors can be used for providing the detection means like the myogenic potential electrometer or the vibration pickup, the same as the above example. Also, even though the continuous swallowing movement measuring device may have any one of the examination means, it is made without departing from the scope of the present invention.

The present invention is not limited to the specifically disclosed embodiment, and variations and modifications may be made without departing from the scope of the present invention.

The present application is based on Japanese priority application No. 2004-229079 filed on Aug. 5, 2004, Japanese priority application No. 2004-255966 filed on Sep. 2, 2004, and Japanese priority application No. 2005-042545 filed on Feb. 18, 2005, the entire contents of which are hereby incorporated by references.

What is claimed is:

1. A continuous swallowing movement measuring device, comprising:
a plurality of pressure sensors placed in a line along a direction of an up and down movement of a thyroid cartilage when a food is swallowed, a first one of the plurality of pressure sensors placed at a top position of the thyroid cartilage, a second one of the plurality of pressure sensors placed along the direction to measure a plurality of swallows included in a continuous swallowing movement; and
a tool for wearing the plurality of pressure sensors and for fixing the plurality of pressure sensors to touch an anterior region of a neck of a subject, wherein
the tool for wearing the plurality of pressure sensors is provided with
fixing means for fixing the plurality of pressure sensors,
a supporter of the plurality of pressure sensors that supports the fixing means,
the supporter having
a stand for holding a jaw;
a sensor mounting part; and
an axle that supports the stand, the axle rotating relative to the sensor mounting part, and
a holding band that holds the supporter of the plurality of pressure sensors on the anterior region of the neck of the subject.

2. The continuous swallowing movement measuring device as claimed in claim 1, wherein a pressure sensor which is placed in a highest position among the plurality of pressure sensors is a sensor to recognize a positioning on an upper limit position or near the upper limit position of the thyroid cartilage at a time of a continuous swallowing movement.

3. The continuous swallowing movement measuring device as claimed in claim 1, wherein the sensor mounting part fixes urethane foam to support the plurality of pressure sensors.

4. A continuous swallowing movement measuring device, comprising:
a plurality of pressure sensors placed in a line along a direction of an up and down movement of a thyroid cartilage when a food is swallowed, a first one of the plurality of pressure sensors placed at a top position of the thyroid cartilage, a second one of the plurality of pressure sensors placed along the direction to measure a plurality of swallows included in a continuous swallowing movement; and
a tool for wearing the plurality of pressure sensors and for fixing the plurality of pressure sensors to touch an anterior region of a neck of a subject, wherein
the tool for wearing the plurality of pressure sensors is provided with
fixing means for fixing the plurality of pressure sensors,
a supporter of the plurality of pressure sensors that supports the fixing means,
the supporter having
a stand for holding a jaw;
a sensor mounting part; and
an axle that supports the stand, the axle rotating relative to the sensor mounting part, and
a holding band that holds the supporter of the plurality of pressure sensors on the anterior region of the neck of the subject, wherein
the continuous swallowing movement measuring device is also provided with
a myogenic potential electrometer that measures a muscle force of a suprahyoid muscle group of the subject, and
a vibration pickup that measures a swallowing sound.

5. A method for a measurement of a continuous swallowing movement, the method comprising:
mounting a tool for wearing a plurality of pressure sensors, which is fixed by touching an anterior region of a neck of a subject, so that a lowest sensor among the plurality of pressure sensors is placed near a thyroid cartilage of the subject, wherein the tool for wearing the plurality of pressure sensors supports the plurality of pressure sensors including pressure sensors recognizing a position of the thyroid cartilage on an upper limit position or near the upper limit position of the thyroid cartilage at a time of a continuous swallowing movement and is provided with the plurality of pressure sensors along a direction of an up and down movement of the thyroid cartilage;
reading changes of an output signal from each of the plurality of pressure sensors during a plurality of swallows included in a continuous swallowing movement when the subject drinks a beverage continuously;
measuring the up and down movement of the thyroid cartilage of the subject when the subject drinks the beverage continuously based on a period of an output signal peak from each of the plurality of pressure sensors; and
evaluating a feeling at a throat at a time of a continuous swallowing of the beverage based on the up and down movement of the thyroid cartilage or the period.

6. The method as claimed in claim 5, wherein the tool for wearing the plurality of pressure sensors is further provided with a supporter of the plurality of pressure sensors,
the supporter having
a stand for holding a jaw,
a sensor mounting part, and
an axle that supports the stand, the axle rotating relative to the sensor mounting part.

7. A method for a measurement of a continuous swallowing movement, the method comprising:
fixing a surface electrode for measuring a myogenic potential by contacting an equivalency region of a mylohyoid muscle of a digastric muscle of an anterior region of a neck of a subject;
obtaining an electric signal which is generated by moving a suprahyoid muscle group from the surface electrode during a plurality of swallows included in a continuous swallowing movement when the subject drinks a beverage continuously; and
evaluating a feeling at a throat at a time of a continuous swallowing of the beverage based on the electric signal obtained from the surface electrode.

8. A method for a measurement of a continuous swallowing movement, the method comprising:
attaching a vibration pickup at a portion located beside a cricoid of an anterior region of a neck of a subject;
measuring a plurality of swallowing sounds from the vibration pickup during a plurality of swallows included in a continuous swallowing movement when the subject drinks a beverage continuously;
measuring a period of a peak of the plurality of swallowing sounds; and
evaluating a feeling at a throat at a time of a continuous swallowing of the beverage based on a period of the plurality of swallowing sounds.

* * * * *